United States Patent
Sun et al.

(10) Patent No.: US 8,183,242 B2
(45) Date of Patent: May 22, 2012

(54) AMINOPYRIMIDINE COMPOUNDS AND THEIR SALTS, PROCESS FOR PREPARATION AND PHARMACEUTICAL USE THEREOF

(75) Inventors: Piaoyang Sun, Lianyungang (CN); Aifeng Lv, Lianyungang (CN); Baohai Yang, Lianyungang (CN); Chunyong Hu, Lianyungang (CN)

(73) Assignees: Piaoyang Sun, Lianyuangang, Jiangsu (CN); Aifeng Lv, Lianyuangang, Jiangsu (CN); Baohai Yang, Lianyuangang, Jiangsu (CN); Chunyong Hu, Lianyuangang, Jiangsu (CN)

( * ) Notice: Subject to any disclaimer, the term of this patent is extended or adjusted under 35 U.S.C. 154(b) by 1120 days.

(21) Appl. No.: 11/794,250

(22) PCT Filed: Dec. 26, 2005

(86) PCT No.: PCT/CN2005/002308
§ 371 (c)(1),
(2), (4) Date: Feb. 19, 2008

(87) PCT Pub. No.: WO2006/069525
PCT Pub. Date: Jul. 6, 2006

(65) Prior Publication Data
US 2008/0312251 A1    Dec. 18, 2008

(30) Foreign Application Priority Data

| Dec. 31, 2004 | (CN) | ............................ 2004 1 0103077 |
| Sep. 30, 2005 | (CN) | ............................ 2005 1 0107402 |

(51) Int. Cl.
C07D 239/42 (2006.01)
C07D 401/04 (2006.01)
C07D 401/14 (2006.01)
C07D 403/02 (2006.01)
A61K 31/505 (2006.01)

(52) U.S. Cl. .................... 514/252.18; 514/275; 544/295; 544/331

(58) Field of Classification Search .................. 544/295, 544/331; 514/252.18, 275
See application file for complete search history.

(56) References Cited

FOREIGN PATENT DOCUMENTS

| CN | 1043531 A | 4/1990 |
| CN | 1218510 A | 6/1999 |
| WO | WO 02/22597 A1 | 3/2002 |
| WO | WO 2004/005281 | 1/2004 |
| WO | WO 2004/029038 | 4/2004 |
| WO | WO 2004/099186 | 11/2004 |
| WO | WO 2004/110452 | 12/2004 |

OTHER PUBLICATIONS

Fabbro et al., Protein Kinases as targets for anticancer agents: from inhibitors to useful drugs, Pharmacology & Therapeutics 93 (2002) 79-88.*
Traxler, Protein Tyrosine Kinase inhibitors in cancer treatment, Expert Opinion on Therapeutic Patents, 7(6): 571-588, 1997.*
Simone, Oncology: Introduction, Cecil Textbook of Medicine, 20th Edition, vol. 1, pp. 1004-1010, 1996.*
Gura et al., Systems for Identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431, 2001.*
Zimmermann, J. et al., "Potent and Selective Inhibitors of the ABL-Kinase: Phenylamino-Pyrimidine (PAP) Derivatives", Bioorganic & Medicinal Chemistry Letters, vol. 7, No. 2, pp. 187-192, 1997.
Zimmermann, J. et al., "Phenylamino-Pyrimidine (PAP)-Derivatives: A New Class of Potent and Highly Selective PDGF-Receptor Autophosphorylation Inhibitors", Bioorganic & Medicinal Chemistry Letters, vol. 6, No. 11, pp. 1221-1226, 1996.

* cited by examiner

*Primary Examiner* — Deepak Rao
(74) *Attorney, Agent, or Firm* — Morris Manning & Martin LLP; Tim Tingkang Xia, Esq.

(57) ABSTRACT

The present invention provides aminopyrimidine compounds of formula (I) and their salts, wherein $R_1$, $R_2$, $R_3$, $R_4$, $R_5$, $R_6$, Q, Z, L, m, n are defined as the description, the methods for preparation thereof, the uses thereof and the pharmaceutical compositions comprising the effective amount of compounds of formula (I). The compounds of formula (I) and their salts can be used as protein kinase inhibitors.

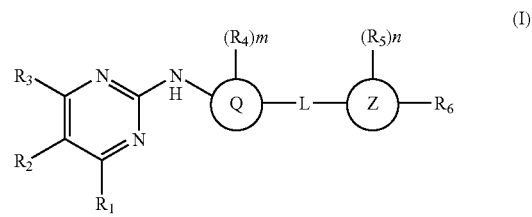

27 Claims, 5 Drawing Sheets

K562 HL-60 control control compoundE0.3μM compoundE10μM compoundF0.03μM compoundF10μM

Imatinib 0.3μM

Imatinib 10μM

AMINOPYRIMIDINE COMPOUNDS AND THEIR SALTS, PROCESS FOR PREPARATION AND PHARMACEUTICAL USE THEREOF

This application is a 371 of PCT/CN05/02308 filed Dec. 26, 2005.

FIELD OF THE INVENTION

The present invention relates to aminopyrimidine compounds of general formula (I) and their salts, a method for the preparation thereof and their uses in treating cell proliferation diseases (e.g. cancers) either independently or in combination with other pharmaceutical compounds.

BACKGROUND ART

More than 95% patients suffering from chronic myelogenous leukemia were found to have chromosome translocation which results in the formation of BCR-ABL fusion protein and thereby the activity of high expression of ABL tyrosine kinase. Accordingly, chronic myelogenous leukemia becomes the therapeutic target of Imatinib. Since human chronic myelogenous leukemia K562 cell expresses Bcr-Abl protein, it is the conventional cell model for studying drugs directing to BCR-ABL.

In the prior art, for example, a recombinant interferon α-2a has been used for the treatment of chronic myelogenous leukemia. This drug exhibits a wide-spectrum in antivirus, antitumor and immune regulation function. Interferon binds with the cell-surface receptors, and thereby induces the generation of a variety of antivirus proteins in the cells to inhibit the growth of virus therein and also strengthen the immune functions, such as enhancing the phagocytosis ability of macrophage and the cell toxicity of lymphocytes toward the target cells, and strengthening the function of natural killer cells.

Recently, Gleevec, namely Imatinib, has been used as the first-line treatment for chronic granulocyte leukemia. However, drug resistance was found in some patients after administration. As reported in some new studies, the second generation of Gleevec may overcome the Gleevec resistance in patients. Gleevec binds with BCR-ABL and hence inhibits the activity of BCR-ABL. BCR-ABL is an enzyme that promotes the growth of the white blood cells. In most cases, mutation of BCR-ABL causes drug resistance, which changes the shape of the enzyme and thereby drugs are not allowed to bind with it. Neil P. Shah and coworkers isolated an imatinib mutant, namely BMS-354825, which exhibits lower selectivity to BCR-ABL enzyme. The experiments were conducted by using mice model with leukemia and the culture of cells from leukemia patient, and the results show that BMS-354825 is more effective than Imatinib. Also, BMS-354825 can overcome most of the Imatinib resistance without showing any significant toxicity. (About 15-20% of Imatinib resistance is originated from another type of mutation, and this new drug is ineffective in these cases). Currently, BMS-354825 has entered phase I clinical trial (*Overriding Imatinib Resistance with a Novel ABL Kinase Inhibitor*, Neil P. Shah, et al.).

Before the discovery of Imatinib, IFN-α, cytosine arabinoside and hereditary hemorrhagic telangiectasia (HHT) are used independently or in combination for the treatment of Philadelphia Chromosome (Ph) positive chronic myelogenous leukemia (CML). Even though these drugs have been widely used, there are still many unsatisfactory effects in using them.

SUMMARY OF THE INVENTION

The objective of the present invention is to provide aminopyrimidine compounds of general formula (I) and their salts, as well as the method for the preparation thereof, and to provide their use in treating cell proliferation diseases (e.g. cancers) either independently or in combination with other pharmaceutical compounds.

The objective of the present invention is achieved by the technical solutions described below. The present invention relates to an aminopyrimidine compound of general formula (I) or the salt thereof:

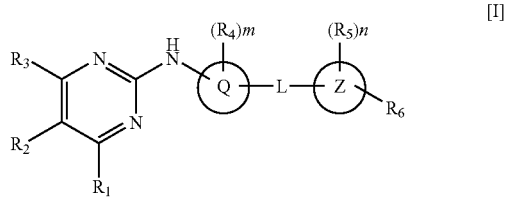

[I]

wherein $R_1$ is selected from substituted or unsubstituted aryl, heteroaryl, or heterocycle, in which the substituent is selected from halogen, $C_{1-4}$ linear or branched alkyl, amino, alkoxy or cycloalkyl;

$R_2$ and $R_3$ are independently selected from hydrogen, halogen, amino, alkylamino, dialkylamino, cyano, nitro, hydroxy, alkoxy, haloalkoxy; or substituted or unsubstituted alkyl, cycloalkyl, alkenyl, alkynyl, aryl, heteroaryl, arylalkyl and heteroarylalkyl, in which the substituent is selected from halogen, $C_{1-4}$ linear or branched alkyl, amino, alkoxy or nitro; or $R_2$ and $R_3$ form 4- to 7-membered, substituted or unsubstituted carbocyclic or heterocyclic ring together with the carbon atoms bound thereto, in which the substituent is selected from halogen, amino, alkylamino, dialkylamino, cyano, nitro, hydroxy, alkoxy, haloalkoxy; $R_4$ is selected from hydrogen, halogen, amino, alkylamino, dialkylamino, cyano; or substituted or unsubstituted alkyl, cycloalkyl, alkenyl, alkynyl, in which the substituent is selected from halogen, amino or hydroxy; $R_5$ is selected from hydrogen, halogen, nitro, cyano, hydroxy, alkoxy, methylenedioxy, haloalkoxy, amino; or substituted or unsubstituted alkyl, cycloalkyl, alkenyl, alkynyl, aryl or heteroaryl, in which the substituent is selected from halogen, amino or hydroxy; $R_6$ is selected from hydrogen, substituted or unsubstituted alkyl, cycloalkyl, aryl, arylalkyl, heteroaryl, heteroarylalkyl, heterocycle, or heterocyclic alkyl, in which the substituent is selected from halogen, amino or $C_{1-4}$ alkyl;

m=0, 1, 2 or 3;

n=0, 1, 2 or 3;

Q is selected from aryl, heteroaryl or heterocyle;

Z is selected from aryl, heteroaryl or heterocycle;

L is selected from:

(1) —$NR_7CO$—,
(2) —$CONR_8$—,
(3) —$NR_9SO_2$—,
(4) —$SO_2NR_{10}$—,
(5) $NR_{11}COO$—,
(6) —$NR_{12}CONR_{13}$—, and
(8) —$OCONR_{14}$—;

wherein $R_7$, $R_8$, $R_9$, $R_{10}$, $R_{11}$, $R_{12}$, $R_{13}$ and $R_{14}$ are each independently selected from hydrogen, substituted or unsubstituted alkyl, substituted or unsubstituted cycloalkyl, in which the substituent is selected from halogen, amino or hydroxyl.

The objective of the present invention is further achieved by the following technical solutions, in which the above-mentioned compound of general formula (I) or the salt thereof is characterized in that $R_1$ is selected from substituted or unsubstituted heteroaryl, preferably substituted or unsubstituted 6-membered heteroaryl, and more preferably substituted or unsubstituted pyridinyl cycle, in which the substituent is selected from halogen, $C_{1-4}$ linear or branched alkyl.

The objective of the present invention is further achieved by the following technical solutions, in which the above-mentioned compound of general formula (I) or the salt thereof is characterized in that $R_2$ and $R_3$ are selected from hydrogen, halogen, amino, alkylamino, cyano, nitro; or substituted or unsubstituted alkyl, cycloalkyl, in which the substituent is selected from halogen; preferably hydrogen or halogen, in which halogen refers to fluorine, chlorine, bromine and iodine atom.

The objective of the present invention is further achieved by the following technical solutions, in which the above-mentioned compound of general formula (I) or the salt thereof is characterized in that $R_4$ is selected from substituted or unsubstituted alkyl, cycloalkyl, alkenyl, alkynyl, preferably substituted or unsubstituted alkyl, and more preferably substituted or unsubstituted $C_{1-4}$ alkyl, in which the substituent is selected from halogen or amino.

The objective of the present invention is further achieved by the following technical solutions, in which the above-mentioned compound of general formula (I) or the salt thereof is characterized in that $R_5$ is selected from hydrogen, halogen, nitro, or substituted or unsubstituted alkyl, cycloalkyl, alkenyl, alkynyl; preferably hydrogen, halogen, or substituted or unsubstituted alkyl, cycloalkyl, in which the substitutent is selected from halogen or hydroxyl.

The objective of the present invention is further achieved by the following technical solutions, in which the above-mentioned compound of general formula (I) or the salt thereof is characterized in that $R_6$ is selected from heteroaryl, heteroarylalkyl, heterocycle, or heterocyclic alkyl, the above groups can be substituted or unsubstituted; preferably substituted or unsubstituted heteroaryl, heterocyclic alkyl, in which the substitutent is preferably $C_{1-4}$ alkyl.

The objective of the present invention is further achieved by the following technical solutions, in which the above-mentioned compound of general formula (I) or the salt is characterized in that m and n are independently selected from 0, 1, 2 or 3.

The objective of the present invention is further achieved by the following technical solutions, in which the above-mentioned compound of general formula (I) or the salt thereof is characterized in that Q is selected from aryl, heteroaryl, or heterocycle, preferably aryl or heteroaryl; and Z is selected from aryl, heteroaryl, or heterocycle, preferably aryl or heteroaryl.

The objective of the present invention is further achieved by the following technical solutions, in which the above-mentioned compound of general formula (I) or the salt thereof is characterized in that L is selected from (1) —$NR_7CO$—, (2) —$CONR_8$—, (3) —$NR_9SO_2$—, (4) —$SO_2NR_{10}$—, or (5) —$NR_{11}COO$—, preferably (1) —$NR_7CO$— or (2) —$CONR_8$—; in which $R_7$, $R_8$, $R_9$, $R_{10}$ and $R_{11}$ are independently selected from alkyl or hydrogen, preferably hydrogen.

The objective of the present invention is further achieved by the following technical solutions, in which the above-mentioned compound of general formula (I) or the salt thereof is characterized in that it may be existed in single enantiomer form of (R), (S), (RS) or (SS), or in enantiomer-enriched form.

The objective of the present invention is further achieved by the following technical solutions, in which the above-mentioned compound of general formula (I) or the salt thereof is characterized in that said compound may form a salt with a amount of acid (e.g. equivalent amount), the acid used in the present invention is selected from organic acid (e.g. acetic acid, trichloroacetic acid, propanoic acid, butanoic acid, aspartic acid, para-toluenesulfonic acid, maleic acid, lactic acid) or inorganic acid (e.g. hydrochloric acid, sulfuric acid, phosphoric acid, methanesulfonic acid), and hydrochloric acid and methanesulfonic acid are preferred.

The objective of the present invention is further achieved by the following technical solutions, in which the above-mentioned compound of general formula (I) or the salt thereof is characterized in that said compound may forms a salt with a amount of a base (e.g. equivalent amount), and the formed salt includes salts of alkali metals (e.g. lithium, sodium, potassium etc.), alkaline earth metals (e.g. magnesium, calcium etc.) or quaternary ammonium (e.g. $NY_4$, in which Y is $C_{1-4}$ alkyl).

The objective of the present invention is further achieved by the following technical solutions, in which the above-mentioned compound of general formula (I) or the salt thereof is characterized in that said compound includes:

4-[(4-methylpiperazin-1-yl)methyl]-N-{6-methyl-5-[(4-(pyrid-3-yl)pyrimid-2-yl)amino]pyrid-3-yl}benzamide;

4-[(4-ethylpiperazin-1-yl)methyl]-N-{6-methyl-5-[(4-(pyrid-3-yl)pyrimid-2-yl) amino]pyrid-3-yl}benzamide;

4-[(4-methylpiperazin-1-yl)methyl]-N-{6-methyl-5-[(4-(pyrid-3-yl)pyrimid-2-yl) amino]pyrid-3-yl}-3-fluorobenzamide;

4-[(4-methylpiperazin-1-yl)methyl]-N-{6-methyl-5-[(4-(pyrid-3-yl)pyrimid-2-yl)amino]pyrid-3-yl}-3-chlorobenzamide;

4-[(4-methylpiperazin-1-yl)methyl]-N-{6-methyl-5-[(4-(pyrid-3-yl)pyrimid-2-yl)amino]pyrid-3-yl}-3-(trifluoromethyl)benzamide;

6-methyl-N-{3-(4-methyl-1H-imidazol-1-yl)-5-(trifluoromethyl)phenyl}-5-[4-(pyrid-3-yl)-2-(pyrimidyl)amino] nicotin;

6-methyl-N-{4-[(4-methylpiperazin-1-yl)methyl]-3-(trifluoromethyl)phenyl}-5-[4-(pyrid-3-yl)-2-(pyrimidyl) amino]nicotin;

4-[(4-methylpiperazin-1-yl)methyl]-N-{5-methyl-4-[(4-(pyrid-3-yl)-2-(pyrimidyl)amino)pyrid-2-yl]-3-(trifluoromethyl)benzamide;

5-methyl-N-[4-(4-methylpiperazin-1-yl)methyl-3-(trifluoromethyl)phenyl]-4-[4-(pyrid-3-yl)-2-(pyrimidyl)amino] pyridinecarboxamide;

5-methyl-N-[3-(4-methyl-1H-imidazol-1-yl)-5-(trifluoromethyl)phenyl]-4-[4-(pyrid-3-yl)-2-(pyrimidyl)amino]pyridinecarboxamide.

The objective of the present invention is further achieved by the following technical solutions. The present invention provides a method for the preparation of the compound of general formula (I) or the salt thereof, which is characterized in that said method includes the following steps:

(A) A compound of general formula (II) reacts with a compound of general formula (III) in basic condition to afford a compound of general formula (IV):

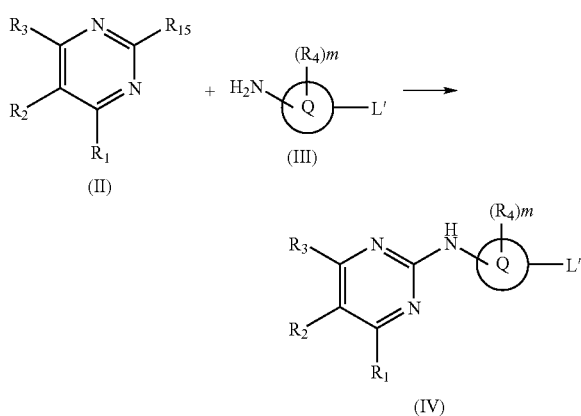

(B) Condensation reaction between the compound of general formula (IV) and a compound of general formula (V) in the presence of a condensation reagent to afford a compound of general formula (I),

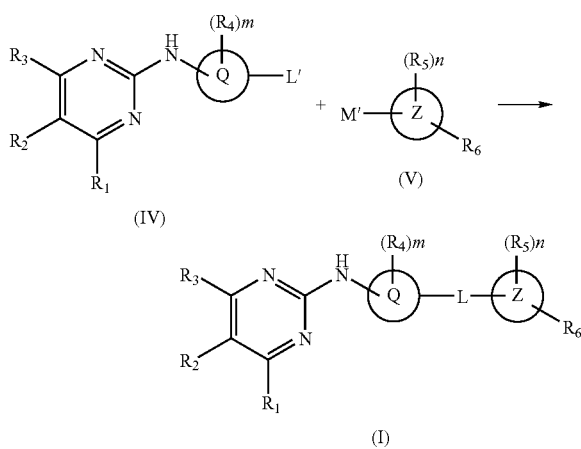

wherein $R_1$, $R_2$, $R_3$, $R_4$, $R_5$, $R_6$, Q, L, m, n are defined as above; L', M' represent groups that allow condensation reaction occurred between them, which include amino, carboxyl, acid anhydride group, ester group, carboxylhalide group, etc., preferably amino, carboxyl or carboxylhalide group; and organic groups, such as nitro and ester group, which can be converted into amino, carboxyl or carboxylhalide group by conventional methods. $R_{15}$ represents easily removable groups, which are selected from halogen (e.g. fluorine, chlorine, bromine, iodine) or methylsulfonyl, ethylsulfonyl, or p-toluenesulfonyl etc.

The objective of the present invention is further achieved by the following technical solutions. The present invention provides a method for the preparation of the compound of general formula (I) or the salt thereof, which is characterized in that said method includes the following steps:

(A) in the preparation of the compound of general formula (IV), the base used in the present invention is selected from organic base (e.g. n-butyllithium, sodium methoxide, sodium ethoxide, potassium tert-butoxide); or inorganic base (e.g. sodium, sodium hydroxide, potassium hydroxide, sodium amide, sodium hydride), and sodium hydride is preferred.

(B) in the preparation of the compound of general formula (I), in the case of condensation reaction occurred between a carboxyl and an amino group, the condensation reagent is selected from N,N-dicyclohexylcarbodiimide, N,N-diisopropylcarbodiimide, N,N-diethylcarbodiimide, mixture of triphenylphosphine and diethyl azodicarboxylate, or mixture of triphenylphosphine and diisopropyl azodicarboxylate etc., and N,N-dicyclohexylcarbodiimide is preferred; in the case of condensation reaction occurred between a carboxylhalide group and an amino group, the condensation reagent is selected from inorganic base (e.g. sodium carbonate, potassium carbonate, calcium carbonate) or organic base (e.g. triethylamine, pyridine, 4-dimethylaminopyridine, tripropylamine, tributylamine), and in which pyridine and triethylamine are preferred.

The objective of the present invention is further achieved by the following technical solutions. The present invention provides the use of said compound or the salt thereof in treating cell proliferation diseases (e.g. cancers) either independently or in combination with other pharmaceutical compounds.

In the present invention, the term "alkyl" refers to a branched or linear saturated aliphatic hydrocarbon group, preferably $C_{1-10}$ branched or linear saturated aliphatic alkyl, such as methyl, ethyl, propyl, i-propyl, butyl, t-butyl, i-butyl, pentyl, hexyl, heptyl, octyl, nonyl, decyl etc.; the term "cycloalkyl" refers to a monocyclic saturated aliphatic hydrocarbon group, preferably $C_3$-$C_{10}$ cycloalkyl, such as cyclopropyl, methyl-cyclopropyl, 2,2-dimethyl-cyclobutyl, ethyl-cyclopentyl, cyclohexyl etc.; for the terms "$C_1$-$C_6$ aralkyl" and "$C_1$-$C_6$ heteroaralkyl", the term "$C_1$-$C_6$" refers to the number of carbon atoms in alkyl moiety.

In the present invention, the term "alkenyl" refers to a $C_{2-10}$ branched, linear or cyclic non-aromatic hydrocarbon group having at least one carbon carbon double bond, such as ethenyl, propenyl, butenyl, cyclohexenyl etc. For the term "$C_{2-6}$ alkenyl", the term "$C_2$-$C_6$" means the number of carbon atom of the alkenyl is 2 to 6.

In the present invention, the term "alkynyl" refers to $C_{2-10}$ branched, linear or cyclic hydrocarbon group having at least one carbon carbon triple bond, such as ethynyl, propynyl, butynyl, 3-methylbutynyl etc. For the term "$C_{2-6}$ alkynyl", the term "$C_2$-$C_6$" means the number of carbon atom of the alkynyl is 2 to 6.

In the present invention, the term "alkoxy" refers to a $C_{1-10}$ cyclic or non-cyclic alkyl with an oxygen atom therein.

In the present invention, the term "aryl" refers to any stable monocyclic or bicyclic rings, wherein each ring comprises up to 7 carbon atoms and at least one is aromatic ring, such as phenyl, naphthyl, tetrahydronaphthyl, biphenyl etc. If the aryl group is a bicyclic ring and one of these rings is non-aromatic, reactions can be conducted with attachment via the aromatic ring.

In the present invention, the term "halogen" refers to fluorine, chlorine, bromine and iodine.

In the present invention, the term "heteroaryl" refers to a stable monocyclic or bicyclic ring, wherein each ring comprises up to 7 carbon atoms and at least one is aromatic ring containing 1 to 4 heteroatom(s), and said heteroatom is selected from O, N and S. In accordance with this definition, "heteroaryl" includes, but not limited to, furanyl, thienyl, pyrrolyl, thiazolyl, thiadiazolyl, isothiazolyl, imidazolyl, triazolyl, triazinyl, pyrazinyl, pyridazinyl, pyridyl, pyrimidyl, benzothienyl, benzofuranyl, indolyl, benzotriazolyl, quinolinyl, quinoxalinyl, isoquinolinyl, tetrahydroquinolinyl etc. As the heteroaryl contains N atoms, "heteroaryl" contains its N-oxide derivative as well. If the heteroaryl is a bicyclic ring and one of these rings is non-aromatic or contains no heteroatoms, reactions can be conducted with attachment via the aromatic ring or via the heteroatom containing ring, respectively.

In the present invention, the term "heterocycle" refers to a monocyclic ring having 4 to 8 atoms, a bicyclic ring having 7 to 12 atoms, or a tricyclic ring having 1 to 16 atoms, in which the ring(s) is consisted of carbon atoms and one or more heteroatoms, and may be saturated or unsaturated, wherein heteroatom is selected from N, O and S, and N and S may be oxidized if N and S are the heteroatoms; N can be ammonium-quaternized if N is the heteroatom. Reactions can be conducted with attachment via any heteroatoms or carbon atoms, provided that the structure thus obtained is stable. When substituents are present in the heterocyclic ring, the substituents may be attached to any atoms on the ring. Examples of the substituents include benzoimidazolyl, benzofuranyl, benzopyrazolyl, benzotriazolyl, benzothiophenyl, carbazolyl, carbolinyl, furanyl, imidazolyl, dihydroindolyl, indolyl, indolazinyl, indazolyl, isobenzofuranyl, isoindolyl, isoquinolyl, isothiazolyl, naphthylpyridyl, pyranyl, pyrazinyl, pyrazolyl, pyridazinyl, pyridopyridyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, hexahydroazapinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisothiazolyl, dihydropyrazinyl, dihydropyrazolyl, dihydropyridyl, dihydropyrimidyl, dihydropyrrolyl, dihydroquinolinyl, dihydrotetrazolyl, dihydrothiadiazolyl, dihydrothiazolyl, dihydrothienyl, dihydrotriazolyl, dihydroazacyclobutyl, methylenedioxybenzoyl, tetrahydrofuranyl, tetrahydrothienyl, thiazinyl, dioxythiadiazinyl, dioxythiadiazoalkyl, isodioxythiadiazolyl etc.; "heterocycle" also includes the following bicyclic compounds, such as imidazo[4,5-b]pyridyl, dihydroimidazo[4,5-b]pyridyl, pyrazolin[4,3-c]pyridyl, dihydropyrazolin[4,3-c]pyridyl, tetrahydropyrazolin[4,3-c]pyridyl, pyrrole[1,2-a]piperazinyl, dihydropyrrole[1,2-a]piperazinyl, tetrahydropyrrole[1,2-a]piperazinyl, cinnolyl, purinyl, 1,6-naphthyridinyl, 1,8-napthyridinyl, imidazo[1,2-a]pyrimidyl, 2,3-dihydroimidazo[2,1-b][1,3]thiazolyl, benzazapinyl dihydrobenazapinyl (dihydroazinyl), benzodiazapinyl, dihydrobenzodiazapinyl, tetrahydrobenzodiazapinyl etc.; "heterocycle" also includes the following three ring compounds, such as phenothiazinyl, carbazolyl, β-carbazolyl, phenazinyl, etc.

Also, the above-mentioned alkyl, alkenyl, alkynyl, cycloalkyl, aryl, heteroaryl and heterocyclyl may be substituted by, but not limited to, the following groups, such as hydroxy, alkyl, haloalkyl, halogen, cyano, nitro, carboxy, ester, amino, alkoxy, alkylamino, dialkylamino, etc.

The compounds and their salts according to the present invention may be administrated orally, transdermally, parenterally (e.g. via injection, inhalation, spray, sublingual, rectum, vagina). "Injection administration" includes intravenous injection, articular injection, intramusclar injection, subcutaneous injection, parenteral injection as well as infusion. Transdermal administration includes local or cross administration. Oral administration is prepared by methods known to a person skilled in the art, such of these formulations may contain one or more adjuvants, such as diluents, sweetening agents, flavoring agents, coloring agents and preserving agents.

Tablets contain the active ingredient in admixture with non-toxic pharmaceutically acceptable excipients. Examples of these excipients include: inert diluents (such as calcium carbonate, sodium carbonate, lactose, calcium phosphate or sodium phosphate), granulating agents or disintegrating agents (such as cornstarch, alginic acid) and binders (such as magnesium stearate, stearic acid, talc). Tablets may be uncoated or coated by known techniques so as to slow down the disintegration and adsorption taken place in the gastrointestinal tract and thereby lengthening the effective time of the drugs to be administrated. For example, glyceryl monostearate or glyceryl distearate may be employed. These compounds may also be prepared in solid, rapidly released form.

Hard capsules contain the active ingredient in admixture with an inert solid diluent, for example, calcium carbonate, calcium phosphate or kaolin whereas soft capsules contain the active ingredient in admixture with water or an oil medium, for example peanut oil, paraffin oil or olive oil.

Aqueous suspensions contain the active ingredient in admixture with pharmaceutical acceptable excipients. Examples of these excipients include suspending agents (such as sodium carboxymethylcellulose, methylcellulose, hydroxypropyl-methylcellulose, sodium alginate, polyvinylpyrrolidone, gum tragacanth, gum acacia), dispersing or wetting agents (which includes naturally-occurring phosphatide, such as lecithin, or condensation products of an alkylene oxide with fatty acid, such as polyoxyethylene stearate, or condensation products (such as heptadecaethyleneoxycetanol) of ethylene oxide with long-chain fatty alcohols or condensation products (such as polyoxyethylene sorbitol monooleate) of ethylene oxide with some esters derived from fatty acids and hexitol or condensation products (such as polyethylene sorbitan monooleate) of ethylene oxide with some esters derived from fatty acids and hexitol anhydrides. The aqueous suspensions may also contain one or more preserving agents (such as ethyl p-hydroxybenzoate, or propyl p-hydroxybenzoate); one or more coloring agents; one or more flavoring agents, and one or more sweetening agents (such as sucrose or saccharin).

Dispersible powders and granules suitable for the preparation of an aqueous suspension are prepared by mixing water, active ingredient and dispersing or wetting agents, suspending agents and one or more preserving agents. Other excipients, such as sweetening agents, flavoring agents and coloring agents, may also be present.

The compounds of general formula (I) of the present invention and their salts may also be used to prepare non-aqueous liquid formulations. Oily suspending agents allow the active ingredients suspended in vegetable oils (such as peanut oil, olive oil, sesame oil) or mineral oils (such as liquid paraffin). Oily suspending agents may contain thickening agent (such as beeswax, hard paraffin or cetyl alcohol), and sweetening agent and flavoring agent may be added to improve the tastiness of the formulations; antioxidants (such as ascorbic acid) may also be added to improve the stability of the formulations.

The compounds of general formula (I) of the present invention and their salts may be used to prepare oil water emulsions. The oil phase is selected from vegetable oils (such as olive oil, peanut oil) or mineral oils (such as liquid paraffin) or mixtures thereof. Emulsifying agents are selected from naturally-occurring gums (such as gum tragacanth or gum acacia) or naturally-occurring phosphatides (such as soybean, lecithin) or some esters (such as sorbitan monooleate) derived from fatty acids and hexitol anhydrides or condensation products (such as polyoxyethylene sorbitan monooleate) of the said esters with ethylene oxide. Emulsions may also contain sweetening agents and flavoring agents.

Sweetening agents in syrups and elixirs are selected from glycerol, propylene glycol, sorbitol or sucrose. These formulations may also contain demulcent, preserving agents and flavoring agents and coloring agents.

The compounds of general formula (I) of the present invention and their salts may be used to prepare suppositories for rectal or vaginal administration. These suppositories are prepared by mixing the active ingredient with suitable non-toxic excipients, which exist as solid at normal temperatures but they melt to liquid in rectal or vaginal environment and thereby release the drug, such as cocoa butter and polyethylene glycols.

The compounds of general formula (I) of the present invention and their salts may also be administered transdermally using methods known to those skilled in the art. For example, mixing a solution or suspension of a compound of formula (I) with penetration enhancing agents and other additives known to those skilled in the art in a volatile solvent, and after sterilization, obtaining the formulation in a specified dosage amount by following known procedures. In addition, after treating with emulsifying agents and water, a solution or suspension of a compound of formula (I) may be formulated into a lotion or ointment.

The solvents used in transdermal delivery systems are known to those skilled in the art, which include lower alcohols (such as ethanol or isopropyl alcohol), lower ketones (such as acetone), lower carboxylates (such as ethyl acetate), polar ethers (such as tetrahydrofuran), lower hydrocarbons (such as n-hexane, cyclohexane or benzene) or halogenated hydrocarbons (such as dichloromethane, chloroform, trichlorotrifluoroethane); and the solvents used in the present invention also include one of the solvents selected from lower alcohols, lower ketones, lower carboxylates, polar ethers, lower hydrocarbons, halogenated lower hydrocarbons, or mixtures thereof.

The penetration enhancing agents used in transdermal delivery systems are known to those skilled in the art, which include monohydroxy or polyhydroxy alcohols (such as ethanol, propylene glycol or benzyl alcohol), saturated or unsaturated $C_8$-$C_{18}$ fatty alcohols (such as lauryl alcohol or cetyl alcohol), saturated or unsaturated $C_8$-$C_{18}$ fatty acids (such as stearic acid), saturated or unsaturated esters with up to 24 carbon atoms (such as those formed from acetic acid, capronic acid, lauric acid, myristic acid, stearic acid, or palmitic acid with methanol, ethanol, propanol, butanol, iso-butanol, sec-butanol, or monoglycerin) or diesters formed from saturated or unsaturated dicarboxylic acids (such as diisopropyl adipate, diisobutyl adipate, diisopropyl sebacate, diisopropyl maleate); penetration enhancing agents may also include phosphatide derivatives (such as lecithin or cephalin), terpenes, amines, ketones, urea and derivatives thereof, and ethers (such as isosorbide dimethyl ether and diethyleneglycol monoethyl ether); Suitable penetration enhancing agents may also include one of the substances selected from monohydroxy or polyhydroxy alcohols, saturated or unsaturated $C_8$-$C_{18}$ fatty alcohols, saturated or unsaturated $C_8$-$C_{18}$ fatty acids, saturated or unsaturated esters with up to 24 carbon atoms, diesters of saturated or unsaturated dicarboxylic acids, phosphatide derivatives, terpenes, amines, ketones, urea and the derivatives thereof, and ethers, or the mixtures thereof.

Binders used in transdermal delivery systems are known to those skilled in the art, which include polyacrylates, silicones, polyurethanes, block polymers, styrene-butadiene coploymers, natural or synthetic rubbers; cellulose, polyethylene derivatives, and silicates may also be used as matrix components. In addition, additives, such as viscous resins or oils may be added to increase the viscosity of the matrix.

For the compounds of general formula (I) of the present invention and their salts, the daily dosage for oral administration is preferably 0.01 to 200 mg/kg; the daily dosage for injection administration (such as intravenous, intramuscular, subcutaneous and parenteral injections or infusion) is preferably 0.01 to 200 mg/kg; the daily rectal or vaginal dosage is preferably from 0.01 to 200 mg/kg; the daily local administration dosage is preferably 0.1 to 200 mg, which is administered once to four times per day; the daily dosage for transdermal administration is preferably 0.01 to 200 mg/kg; the daily inhalation dosage is preferably 0.01 to 10 mg/kg, wherein "mg" refers to the weight of the active ingredient present in the pharmaceutical composition, and "kg" refers to the total body weight of the patient.

It is appreciated by those skilled in the art that drug dosage is depended on a variety of factors, which include, but not limited to, the following factors: the activity of the specific compound employed, age of patient, body weight of patient, health status of patient, gender of patient, diet of patient, time of administration, route of administration, excretion rate, drug combinations etc.; and also the best way of treatment such as the mode of treatment and the daily dosage of compounds of formula (I) or pharmaceutically acceptable salts thereof may be determined by those skilled in the art using conventional treatment regimen.

In one aspect, the present invention provides the use of the compounds of the present invention and their salts in treating cell proliferation diseases (e.g. cancers) either independently or in combination with other pharmaceutical compounds. Antitumor agents that can be used in combination with the compounds of the present invention and the salts thereof include polynucleotides, polypeptides, biomimetic drugs, alkaloids, alkylating agents, antitumor antibiotics, antimetabolites, hormones, platinum compounds, monoclonal antibodies conjugated with antitumor drugs, toxins, and/or radionuclides, biological response modifiers (e.g. interferons), immunotherapy agents, hematopoietic growth factors, gene therapy reagents, antisense therapy reagents, nucleotides, antitumor vaccines etc. Antitumor agents are preferably apoptosis inducing agents or apoptosis stimulating agents. Apoptosis inducing agents include, but not limited to, radiogens, kinase inhibitors (e.g. epidermal growth factor receptor kinase inhibitors, vascular growth factor receptor kinase inhibitors, platelet-derived growth factor receptor kinase inhibitors and Bcr-abl kinase inhibitors such as STI-157, Gleevec), and preferably antisense molecules, antibodies (e.g. Herceptin and Rituxan), anti-estrogens (e.g., raloxifene and tamoxifen), anti-androgens (e.g. flutamide, bicalutamide, finasteride, amino-glutethamide, ketoconazole, and corticosteroids), COX-2 inhibitors (e.g. Celecoxib, meloxicam, NS-398), non-steroidal anti-inflammatory drugs and cancer chemotherapeutic drugs (e.g., irinotecan), CPT-11, fludarabine, dacarbazine, dexabethasone, mitoxantrone, Mylotarg, VP-16, cisplatinum, 5-FU, Doxrubicin, TAXOTERE, cell labeled molecules, ceramide, cytokine, staurosprine, and the like.

The present invention relates to a method for the preparation of compounds of formula (I) and their salts. Specifically, said method includes:

Stage A: This stage includes the reaction between compound (II) and compound (III) to produce compound (IV). The reaction is conducted in basic condition and the base employed is selected from organic base (such as pyridine, triethylamine, hexahydropyridine, N-methylpiperazine, 4-dimethylaminopyridine) or inorganic base (such as sodium carbonate, potassium carbonate, sodium bicarbonate, potassium bicarbonate, sodium methoxide, sodium ethoxide, sodium amide, sodium hydride, and n-butyllithium etc). The base employed is limited to the amount of 1~10 times of the weight of compound (II), and preferably 1 to 3 times; the reaction temperature ranges from −80□ to 100□ and preferably from 0□ to 60□; the reaction time depends on the types of compound (II) and compound (III), the solvent employed and the reaction temperature etc., which is typically limited to the range from 1 min to 72 hrs, and preferably from 15 min to 24 hrs.

Stage B: This stage includes the reaction between compound (IV) and compound (V) to produce compound (I). When the condensation reaction is conducted between an acid and an amine, the condensation reagent is selected from N,N-dicyclohexylcarbodiimide, N,N-diisopropylcarbodiimide, N,N-diethylcarbodiimide, mixture of triphenylphosphine and diethyl azodicarboxylate, and mixture of triphenylphosphine and diisopropyl azodicarboxylate etc., preferably N,N-dicyclohexylcarbodiimide. The solvent employed is selected from toluene, benzene, dichloromethane, chloroform, tetrahydrofuran, or the mixture of the above solvents, preferably dichloromethane. The reaction temperature is limited to the range from −80° C. to 100° C., and preferably from 0° C. to 60° C. The reaction time depends on the types of compound (IV) and compound (V), the solvent employed and the reaction temperature etc., which is typically limited to the range from 1 min to 72 hrs, and preferably from 15 min to 24 hrs. When the condensation reaction is conducted between a carboxylhalide and an amine, the base is selected from organic base (such as pyridine, triethylamine, hexahydropyridine, N-methylpiperazine, 4-dimethylaminopyridine) or inorganic base (such as sodium carbonate, potassium carbonate, sodium bicarbonate, potassium bicarbonate, sodium methoxide, sodium ethoxide, sodium amide, sodium hydride, n-buthyllithium etc). The base employed is limited to the amount of 1~10 times of the weight of compound (IV), and preferably 1 to 3 times. The reaction temperature ranges from −80° C. to 100° C. and preferably from 0° C. to 60° C. The reaction time depends on the types of compound (II) and compound (III), the solvent employed and the reaction temperature etc., which is typically limited to the range from 1 min to 72 hrs, and preferably from 15 min to 24 hrs.

BRIEF DESCRIPTION OF THE DRAWING

FIG. 3a: Control diagram of human myeloid leukemia K562 cells.

FIG. 3b: Control diagram of promyelocytic leukemia HL-60.

FIG. 3c: Inhibition diagram of HH-GV-E (0.3 uM) on the proliferation of human myeloid leukemia K562 cells.

FIG. 3d: Inhibition diagram of HH-GV-E (10 uM) on the proliferation of promyelocytic leukemia HL-60.

FIG. 3e: Inhibition diagram of HH-GV-F (0.03 uM) on the proliferation of human myeloid leukemia K562 cells.

FIG. 3f: Inhibition diagram of HH-GV-F (10 uM) on the proliferation of promyelocytic leukemia HL-60.

FIG. 3g: Inhibition diagram of Imatinib (0.3 uM) on the proliferation of human myeloid leukemia K562 cells.

FIG. 3h: Inhibition diagram of Imatinib (10 uM) on the proliferation of promyelocytic leukemia HL-60.

PREFERRED EMBODIMENTS OF THE INVENTION

Figure 1:
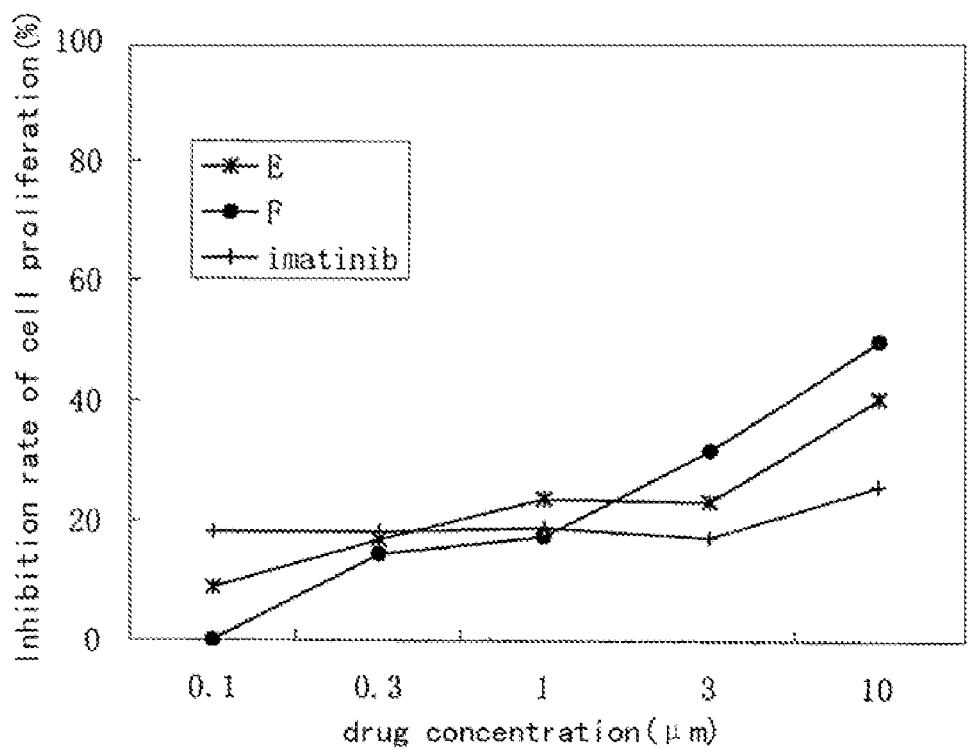
FIG. 1 shows the correlation of the drug concentration of the aminopyrimidine compounds with the inhibition rate of the proliferation of promyelocytic leukemia HL-60.

The following examples are provided so that the invention might be more fully understood. These examples are for illustration only and should not be construed as limiting the invention in any way.

The invention is illustrated by the following examples:

EXAMPLE 1:

Preparation of N-(5-nitro-2-methylpyrid-3-yl)-4-(pyrid-3-yl)-2-pyrimidinamine

To a stirred solution of 2-methylsulfonyl-4-(pyridin-3-yl) pyrimidine (3.0 g) and 2-methyl-3-amino-5-nitropyridine (5.0 g) in DMF (50 mL) at 0-5° C. was added sodium hydride (60%, 2.3 g). The reaction mixture was naturally warmed to room temperature and stirred for 6 hours. Chloroform (50 mL) and water (50 mL) were added to the reaction and the phases were separated, the aqueous phase was extracted with Chloroform (2×100 mL). The organic extracts were combined, dried, filtered, concentrated and the residue was purified by chromatography to provide_N-(5-nitro-2-methylpyrid-3-yl)-4-(pyrid-3-yl)-2-pyrimidinamine (5.2 g).

EXAMPLE 2:

Preparation of N-(5-amino-2-methylpyrid-3-yl)-4-(pyrid-3-yl)-2-pyrimidinamine
Method A To a stirred solution of N-(5-nitro-2-methylpyrid-3-yl)-4-(pyrid-3-yl)-2-pyrimidinamine (3.0 g) in methanol (100 mL) was added activated nickel (0.3 g). Hydrogen was added to the reaction mixture at atmospheric pressure till the starting material disappeared. The solid was filtered off and the filtrate was concentrated to give the N-(5-amino-2-methylpyrid-3-yl)-4-(pyrid-3-yl)-2-pyrimidinamine (2.8 g).
Method B To a stirred solution of N-(5-nitro-2-methylpyrid-3-yl)-4-(pyrid-3-yl)-2-pyrimidinamine (18.0 g) and hydrazine hydrate (9 mL) in ethanol (180 mL) was added activated nickel (0. g). The mixture was refluxed for 3 hours, filtered and the filtrate was concentrated in vacuo to give solid, which was put in the fridge (0° C.) overnight. The residue was filtrated off and the filtrate was concentrated in vacuo to give N-(5-amino-2-methylpyrid-3-yl)-4-(pyrid-3-yl)-2-pyrimidinamine (15 g).

Method C

To a flask was added N-(5-nitro-2-methyl-pyrid-3-yl)-4-(pyrid-3-yl)-2-pyrimidinamine (18.0 g) and THF (200 mL) and the solution was cooled to 0-5° C. To the solution was added LiAlH$_4$ (about 2.2 g in total) in several portions and the mixture was stirred for 2 hours at the same temperature. The reaction mixture was acidified to pH=5-6 using 1N HCl and then extracted with CH$_2$Cl$_2$ (2×100 mL). The organic extracts were combined, dried, filtrated and concentrated to afford N-(5-amino-2-methylpyrid-3-yl)-4-(pyrid-3-yl)-2-pyrimidinamine (12 g).

EXAMPLE 3:

Preparation of 4-[(4-methylpiperazin-1-yl)methyl]-N-{6-methyl-5-[(4-(pyrid-3-yl)pyrimid-2-yl)amino]pyrid-3-yl}benzamide
Method D To a flask was added 4-((4-methylpiperazin-1-yl)methyl)benzoic acid (3.2 g) and SOCl$_2$ (100 mL) and the solution was refluxed for 4 hours. The reaction mixture was concentrated under reduced pressure to give a solid, which was used for the next step directly.

To the above carboxylic acid chloride was dropped a clear solution of N-(5-amino-2-methylpyridin-3-yl)-4-(3-pyridyl)pyrimidin-2-amine (3.0 g) in pyridine (80 mL) and the solution was stirred at room temperature overnight. The solvent was removed under reduced pressure, and then the residue was added with chloroform (100 mL) and water (100 mL) for extraction. The organic phase was dried, filtrated, concentrated, and purified through column chromatography to give 4-[(4-methylpiperazin-1-yl)methyl]-N-{6-methyl-5-[(4-(pyrid-3-yl)pyrimid-2-yl)amino]pyrid-3-yl}benzamide (4.2 g).
Method E To a flask was added 4-((4-methylpiperazin-1-yl)methyl)benzoic acid (3.2 g), dicyclohexylcarbodiimide (3.0 g), N-(5-amino-2-methylpyridin-3-yl)-4-(3-pyridyl)pyrimidin-2-amine (3.0 g) and CH$_2$Cl$_2$ (100 mL) and the reaction mixture was stirred at room temperature overnight. The reaction mixture was filtrated and the filtrate was washed with water (100 mL×2), dried, filtrated, concentrated, and purified through column chromatography to give 4-[(4-methylpiperazin-1-yl)methyl]-N-{6-methyl-5-[(4-(pyrid-3-yl)pyrimid-2-yl)amino]pyrid-3-yl}benzamide (4.0 g).

EXAMPLE 4:

Preparation of 4-[(4-methylpiperazin-1-yl)methyl]-N-{6-methyl-5-[(4-(pyrid-3-yl)pyrimid-2-yl)amino]pyrid-3-yl}benzamide methanesulfonic acid salt
Method F To a flask was added 4-[(4-methylpiperazin-1-yl) methyl]-N-{6-methyl-5-[(4-(pyrid-3-yl)pyrimid-2-yl)amino]pyrid-3-yl}benzamide (2.0 g), methanesulfonic acid (0.40 g) and purified water (100 mL). After the solution was clear, the reaction mixture was filtrated and the filtrate was freeze-dried to give 4-[(4-methylpiperazin-1-yl)methyl]-N-{6-methyl-5-[(4-(pyrid-3-yl)pyrimid-2-yl)amino]pyrid-3-yl} benzamide methanesulfonic acid salt (2.2 g).
Method G To a flask was added 4-[(4-methylpiperazin-1-yl)methyl]-N-{6-methyl-5-[(4-(3-pyridyl)-2-pyrimidyl)amino]-3-pyridyl}benzamide (2.0 g), methanesulfonic acid (0.40 g) and methanol (100 mL). After the solution was clear, the reaction mixture was concentrated under reduced pressure to about 20 mL and acetone was added to get a crystal. Filtrated and the solid was dried to give 4-[(4-methylpiperazin-1-yl)methyl]-N-{6-methyl-5-[(4-(pyrid-3-yl)pyrimid-2-yl)amino]pyrid-3-yl} benzamide methanesulfonic acid salt (2.0 g).

EXAMPLE 5:

Preparation of 4-[(4-ethylpiperazin-1-yl)methyl]-N-{6-methyl-5-[(4-(pyrid-3-yl)pyrimid-2-yl)amino]pyrid-3-yl}benzamide The title compound was prepared using the same method as method D or E of Example 3, except that 4-((4-methylpiperazin-1-yl)methyl)benzoic acid (3.2 g) was replaced with 4-((4-ethylpiperazin-1-yl)methyl)benzoic acid (3.3 g).

EXAMPLE 6:

Preparation of 4-[(4-ethylpiperazin-1-yl)methyl]-N-{6-methyl-5-[(4-(pyrid-3-yl)pyrimid-2-yl)amino]pyrid-3-yl}benzamide methanesulfonic acid salt The title compound was prepared using the same method as method F or G of Example 4, except that 4-[(4-methylpiperazin-1-yl)methyl]-N-{6-methyl-5-[(4-(pyrid-3-yl)pyrimid-2-yl)amino]pyrid-3-yl}benzamide (2.0 g) was replaced with 4-[(4-ethylpiperazin-1-yl)methyl]-N-{6-methyl-5-[(4-(pyrid-3-yl)pyrimid-2-yl)amino]pyrid-3-yl} benzamide (2.10 g).

EXAMPLE 7:

Preparation of 4-[(4-methylpiperazin-1-yl)methyl]-N-16-methyl-5-[(4-(pyrid-3-yl) pyrimid-2-yl)amino]pyrid-3-yl-3-fluorobenzamide The title compound was prepared using the same method as method D or E of Example 3, except that 4-((4-methylpiperazin-1-yl)methyl)benzoic acid (3.2 g) was replaced with 4-((4-methylpiperazin-1-yl)methyl)-3-fluoro-benzoic acid (3.3 g).

EXAMPLE 8:

Preparation of 4-[(4-methylpiperazin-1-yl)methyl]-N-{6-methyl-5-[(4-(pyrid-3-yl)pyrimid-2-yl)amino]pyrid-3-yl}-3-fluorobenzamide methanesulfonic acid salt The title compound was prepared using the same method as method F or G of Example 4, except that 4-[(4-methylpiperazin-1-yl)methyl]-N-{6-methyl-5-[(4-(pyrid-3-yl)pyrimid-2-yl)amino]pyrid-3-yl}benzamide (2.0 g) was replaced with 4-[(4-methylpiperazin-1-yl)methyl]-N-{6-methyl-5-[(4-(pyrid-3-yl)pyrimid-2-yl)amino]pyrid-3-yl}-3-fluorobenzamide (2.10 g).

EXAMPLE 9:

Preparation of 4-[(4-methylpiperazin-1-yl)methyl]-N-{6-methyl-5-[(4-(pyrid-3-yl)pyrimid-2-yl)amino]pyrid-3-yl}-3-chlorobenzamide The title compound was prepared using the same method as method D or E or Example 3, except that 4-((4-methylpiperazin-1-yl)methyl)benzoic acid (3.2 g) was replaced with 4-((4-methylpiperazin-1-yl)methyl)-3-chloro-benzoic acid (3.4 g).

EXAMPLE 10:

Preparation of 4-[(4-methylpiperazin-1-yl)methyl]-N-{6-methyl-5-[(4-(pyrid-3-yl)-2-(pyrimidyl)amino)pyrid-3-yl]-3-chlorobenzamide methanesulfonic acid salt The title compound was prepared using the same method as method F or G of Example 4, except that 4-[(4-methylpiperazin-1-yl)methyl]-N-{6-methyl-5-[(4-(pyrid-3-yl)pyrimid-2-yl)amino]pyrid-3-yl}benzamide (2.0 g) was replaced with 4-[(4-methylpiperazin-1-yl)methyl]-N-{6-methyl-5-[(4-(pyrid-3-yl)pyrimid-2-yl)amino]pyrid-3-yl}-3-chlorobenzamide (2.20 g).

EXAMPLE 11:

Preparation of 4-[(4-methylpiperazin-1-yl)methyl]-N-{6-methyl-5-[(4-(pyrid-3-yl)pyrimid-2-yl)amino]pyrid-3-yl}-3-(trifluoromethyl)benzamide The title compound was prepared using the same method as method D or E of Example 3, except that 4-((4-methylpiperazin-1-yl)methyl)benzoic acid (3.2 g) was replaced with 4-((4-methylpiperazin-1-yl)methyl)-3-(trifluoromethyl)benzoic acid (3.6 g).

EXAMPLE 12:

Preparation of 4-[(4-methylpiperazin-1-yl)methyl]-N-{6-methyl-5-[(4-(pyrid-3-yl)pyrimid-2-yl)amino]pyrid-3-yl}-3-(trifluoromethyl)benzamide methanesulfonic acid salt The title compound was prepared using the same method as method F or G of Example 4, except that 4-[(4-methyl-1-piperazinyl)methyl]-N-{6-methyl-5-[(4-(3-pyridyl)-2-pyrimidyl)amino]-3-pyridyl}benzamide (2.0 g) was replaced with 4-[(4-methyl-1-piperazinyl)methyl]-N-{6-methyl-5-[(4-(3-pyridyl)-2-pyrimidyl)amino]-3-pyridyl}-3-(trifluoromethyl)benzamide (2.35 g).

EXAMPLE 13:

Preparation of 6-methyl-N-{3-(4-methyl-1H-imidazol-1-yl)-5-(trifluoromethyl)phenyl}-5-[4-(pyrid-3-yl)pyrimid-2-yl-amino]nicotin
Method I To a flask was added 6-methyl-5-[4-(pyrid-3-yl)pyrimid-2-yl-amino]nicotinic acid (30.7 g, 0.1 mol), 3-(4-methyl-1H-imidazol-1-yl)-5-(trifluoromethyl)aniline (24.1 g, 0.1 mol), triethylamine (83 mL) and DMF (800 mL) and the mixture was cooled to 10° C. To the mixture was added dropwisely a mixture of propylphosphoric anhydride and DMF (1:1, 87.5 mL) and then the reaction was stirred for 24 hours at room temperature. To the reaction solution was added saturated ammonium chloride solution, and extracted with ethyl acetate for three times. The combined organic phases were dried, filtered, concentrated, and purified through column chromatography to give the title compound.
Method II To a flask was added 6-methyl-5-[4-(pyrid-3-yl)pyrimid-2-ylamino) nicotinic acid (30.7 g) and SOCl$_2$ (500 mL) and the reaction mixture was refluxed for 4 hours. The reaction mixture was concentrated under reduced pressure to give a solid, which is used for the next step directly.

To the above acid chloride was added a clear solution of 3-(4-methyl-1H-imidazol-1-yl)-5-(trifluoromethyl)aniline (24.1 g) in pyridine (200 mL) and the reaction mixture was stirred at room temperature overnight. The solvent was removed under reduced pressure, and then the residue was added with chloroform (500 mL) and water (500 mL) and extracted. The organic phase was dried, filtrated, concentrated, and purified through column chromatography to give the titled compound.
Preparation of the Intermediate 3-(4-methyl-1H-imidazol-1-yl)-5-(trifluoromethyl)aniline:

To a flask was added 3-fluoro-5-(trifluoromethyl)benzonitrile (17 g, 89 mmol), 4-methylimidazole (22.2 g, 270 mmol), N,N-dimethylacetamide (80 mL) and the reaction mixture was stirred at 145° C. for 19 hours. The solvent was removed under reduced pressure and ethyl acetate (200 mL) was added. The solution was washed with brine (2×200 mL), dried, filtered, concentrated and recrystallized from ethyl ether and petroleum ether to give an intermediate: 3-(4-methyl-1H-imidazol-1-yl)-5-(trifluoromethyl)benzonitrile.

To a flask was added the intermediate of the previous step (16.7 g, 66 mmol), 1,4-dioxane (300 mL) and 1M NaOH aqueous solution (275 mL) and the reaction mixture was stirred at 95° C. for 18 hours. After the solvent was removed by concentration, the reaction mixture was neutralized by 1N HCl, and then extracted with n-butanol (250 mL×2). The organic phase was dried and concentrated to give a intermediate: 3-(4-methyl-1H-imidazol-1-yl)-5-(trifluoromethyl)benzoic acid.

To a solution of the intermediate of the previous step (6.8 g, 25 mmol) in t-butanol (200 mL) was added triethylamine (5.23 mL, 37.5 mmol) and diphenyl phosphoryl azide (DPPA) (7.6 g, 27.5 mmol) and the reaction mixture was stirred at 80° C. for 16 hours. The solvent was removed under reduced pressure and water (100 mL) was added. The solution was extracted with ethyl acetate (2×100 mL) and the combined organic phase was washed with brine, dried, filtered, concentrated, purified through column chromatography, and recrystallized from ethyl ether and petroleum ether to give an intermediate: 3-(4-methyl-1H-imidazol-1-yl)-5-(trifluoromethyl)-N-(tert-butoxycarbonyl) aniline.

To a flask was added the intermediate of the previous step (5 mmol) and HCl/isopropanol (30 mL, 4M) and the reaction mixture was stirred at 60° C. for 5 hours. The solvent was removed under reduced pressure and saturated sodium bicarbonate solution (80 mL) was added. The solution was extracted with ethyl acetate (3×80 mL) and the combined organic phase was washed with brine, dried, filtered, concentrated and recrystallized from ethyl ether and petroleum ether to give the intermediate 3-(4-methyl-1H-imidazol-1-yl)-5-(trifluoromethyl)aniline.

EXAMPLE 14:

Preparation of 6-methyl-N-{4-[(4-methylpiperazin-1-yl)methyl]-3-(trifluoromethyl)phenyl}-5-[4-(pyrid-3-yl)-2-(pyrimidyl)amino]nicotin The title compound was prepared using the same method as method I or II of Example 13, except that 3-(4-methyl-1H-imidazol-1-yl)-5-(trifluoromethyl)aniline (20.7 g, 0.1 mol) was replaced with 4-(4-methylpiperazin-1-yl)-3-(trifluoromethyl)aniline (25.9 g, 0.1 mol).
Preparation of the Intermediate 4-(4-methylpiperazin-1-yl)-3-(trifluoromethyl)aniline:

To a solution of 2-bromo-4-nitrotoluene (23.2 mmol) in NMP (200 mL) was added sodium trifluoroacetate (8.5 g, 62.5 mmol) and CuI (8.75 g, 46 mmol) and the reaction mixture was stirred at 160° C. for 4 hours. The solution was cooled and water (300 mL) was added. The solution was filtrated and the solid was washed with ethyl ether (250 mL×3). The organic phase was washed with water and brine, dried, filtered, concentrated and purified through column chromatography to give 2-(trifluoromethyl)-4-nitrotoluene (3.12 g).

To a mixture of the intermediate of the previous step (0.5 g, 2.44 mmol) and acetic acid (1.9 mL) was added NBS (0.651 g, 3.66 mmol) and benzoyl peroxide (6 mg, 0.024 mmol) and the reaction mixture was refluxed overnight. After the solution was cooled, the solvent was removed under reduced pressure. Ethyl acetate and saturated sodium bicarbonate solution were added and the organic phase was dried, filtered, concentrated to give a intermediate: 1-(bromomethyl)-4-nitro-2-(trifluoromethyl)benzene.

To a mixture of the intermediate of the previous step (400 g) and $CH_2Cl_2$ (2800 mL) was added triethylamine (197 mL) and N-methylpiperazine (157 mL, 1.41 mmol) and the mixture was stirred at room temperature for 2 hours. Then saturated sodium bicarbonate solution was added and the organic phase was separated, dried, filtered, concentrated and purified through column chromatography to give a intermediate: 1-[4-nitro-2-(trifluoromethyl)benzyl]-4-methylpiperazine.

To a flask was added the intermediate of the previous step (3.0 g), activated nickel (0.3 g) and methanol (100 mL), and then hydrogen was added to the mixture at atmospheric pressure till the starting material disappeared. Filtered, concentrated and purified through column chromatography to give 4-(4-methylpiperazin-1-yl)-3-(trifluoromethyl)aniline.

EXAMPLE 15:

Preparation of 4-[(4-methylpiperazin-1-yl)methyl]-N-{5-methyl-4-[(4-(pyrid-3-yl)pyrimid-2-yl)amino]pyrid-2-yl}-3-(trifluoromethyl)benzamide To a flask was added N-(4-amino-5-methylpyridin-2-yl)-4-[(4-methylpiperazin-1-yl)methyl]-3-(trifluoromethyl)benzamide (7.1 g), 2-mesyl-4-(3-pyridyl)pyrimidine (5.0 g) and DMF (50 mL). After the solution was cooled to about 0° C., sodium hydride (60%, 1.5 g) was added in several portions and the reaction was stirred at the same temperature for 2 hours, then warmed up to room temperature for 1 hour. A mixture solvent of chloroform/methanol (30:1, 100 mL) was added and the PH value was adjusted to 7 using 10% citric acid. The aqueous phase was extracted, then the organic combined phase was washed with brine, dried, filtered, concentrated and Purified through column chromatography to give the title compound.

Preparation of N-(4-amino-5-methylpyridin-2-yl)-4-[(4-methylpiperazin-1-yl)methyl]-3-(trifluoromethyl)benzamide:

To a solution of 2-chloro-5-methylpyridine (10 g) in acetic anhydride (50 mL) was added 30% $H_2O_2$ (50 mL) in several portions and the reaction mixture was stirred at room temperature for 24 hours, then stirred at 60° C. for 30 hours. The excess acetic acid was removed under reduced pressure and concentrated $H_2SO_4$ (30 mL) was added to the residue. The solution was poured into a mixture solution of nitric acid (50 mL) and concentrated $H_2SO_4$ (30 mL) and the reaction mixture was stirred at 100° C. for half hour. The reaction was then poured into ice-water and was basified by using solid ammonium carbonate and ammonia. Filtered to give an intermediate: 2-chloro-4-nitro-5-methyl-pyridine-N-oxide.

To a flask was added the intermediate of the previous step (1.0 g) and 10% ammonia/ethanol (20 mL) and the solution was refluxed in a high pressure autoclave for 4 hours. Cooled down and ethanol was removed under reduced pressure. Water was added. After filtration, the solid was recrystallized from water to provide an intermediate: 2-amino-4-nitro-5-methyl-pyridine-N-oxide.

To a flask was added the intermediate of the previous step (13.4 g, 71 mmol) and chloroform (150 mL) and the reaction mixture was cooled to 0-5° C. $PCl_3$ (19 mL) was added and the mixture was stirred at 70-80° C. for 1 hour. Cooled down and water was added. The reaction mixture was basified by using sodium hydroxide solution and extracted with chloroform. The combined organic phase was washed with brine, dried, filtered, concentrated and recrystallized from petroleum ether to give an intermediate: 2-amino-4-nitro-5-methylpyridine.

To a flask was added 4-[(4-methylpiperazin-1-yl)methyl)-3-(trifluoromethyl) benzoic acid (3 g, 10 mmol) and thionyl chloride (50 mL) and the reaction mixture was refluxed for 5 hours. The solvent was removed under reduced pressure and the remained thionyl chloride was removed by azeotrope with dry toluene twice.

To the acid chloride was added pyridine (50 mL), and 2-amino-4-nitro-5-methylpyridine (1.53 g, 10 mmol) was added under stirring. The mixture was stirred at room temperature overnight. The solvent was removed under reduced pressure and water was added. The PH value was justified to 8 by using saturated sodium bicarbonate solution and extracted with chloroform. The combined organic phase was dried, filtered, concentrated and purified through column chromatography to give an intermediate: N-(4-nitro-5-methylpyridin-2-yl)-4-[(4-methylpiperazin-1-yl)methyl]-3-(trifluoromethyl)benzamide.

To a flask was added the intermediate of the previous step (5.0 g, 10 mmol), hydrazine hydrate (5.4 mL), methanol (180 mL) and a small amount of Raney-Nickel and the mixture was refluxed for 4 hours. The mixture was filtrated and the filtrate was concentrated under reduced pressure. The residue was dried by azeotrope with toluene and then treated with $CH_2Cl_2$, filtered and dried to give N-(4-amino-5-methylpyridin-2-yl)-4-[(4-methylpiperazin-1-yl)methyl]-3-(trifluoromethyl)benzamide.

EXAMPLE 16:

Preparation of 5-methyl-N-[4-((4-methylpiperazin-1-yl)methyl-3-(trifluoromethyl)phenyl)-4-[4-(pyrid-3-yl)-2-(pyrimidyl)amino]pyridinecarboxamide The title compound was prepared using the same method as method I or II of Example 13, except that 6-methyl-5-[4-(pyrid-3-yl)pyrimid-2-ylamino]nicotinic acid (30.7 g, 0.1 mol) was replaced by 5-methyl-4-[(4-(pyrid-3-yl)pyrimid-2-ylamino]picolinic acid (30.7 g, 0.1 mol); and 3-(4-methyl-1H-imidazol-1-yl)-5-(trifluoromethyl)aniline (24.1 g, 0.1 mol) was replaced by 4-(4-methylpiperazin-1-yl)-3-(trifluoromethyl)aniline (25.9 g, 0.1 mol).

EXAMPLE 17:

Preparation of 5-methyl-N-[3-(4-methyl-1H-imidazol-1-yl)-5-(trifluoromethyl)phenyl]-4-[4-(pyrid-3-yl)-2-(pyrimidyl)amino]pyridinecarboxamide The title compound was prepared using the same method as method I or II of Example 13, except that 6-methyl-5-[4-(pyrid-3-yl)pyrimid-2-ylamino]nicotinic acid (30.7 g, 0.1 mol) was replaced by 5-methyl-4-[4-(pyrid-3-yl)pyramid-2-ylamino)picolinic acid (30.7 g, 0.1 mol).

EXAMPLE 18:

| Compound F | 400 g |
|---|---|
| Starch | 100 g |
| Sucrose | 20 g |
| Microcrystalline cellulose | 10 g |
| 0.5% CMC solution | Adequate amount |
| Magnesium Stearate | 5 g |
| | 1000 Tablets |

Granulated by conventional wet method, tabletted and packaged.

Test Example 1:

In Vitro Test for the Antitumor Activities of HH-GV-E, HH-GV-F and Gleevec

HH-GV-E refers to 4-((4-methylpiperazin-1-yl)methyl)-N-[6-methyl-5-[[4-(pyrid-3-yl)pyrimidin-2-yl]amino]pyrid-3-yl]-3-chloro-benzamide methanesulfonic acid salt.

HH-GV-F refers to 4-((4-methylpiperazin-1-yl)methyl)-N-[6-methyl-5-[[4-(pyrid-3-yl)pyrimidin-2-yl]amino]pyrid-3-yl]-3-(trifluoromethyl)-benzamide methanesulfonic acid salt.

1) Cell Strain

HL-60: human acute promyelocytic leukemia Cell. The expression of Bcr-Abl tyrosine kinase is negative.

K562: human chronic myelogenous leukemia cell, expressing $P^{210}$ Bcr-Abl tyrosine kinase.

2) Test Agents, Drugs, and Equipments

RPMI-1640, DMEM supplied by Gibico BRL corporation; fetal bovine serum supplied by Hyclone corporation; ELIASA: POLAR star type, manufactured by German BMG corporation; MTT, supplied by Sigma.

3) Methods

Main steps of MTT assay:

Cells were grown in a medium containing 10% fetal bovine serum and were kept in the logarithmic growth phase.

Test cells were inoculated in 96-well plate with an initial density of $4 \times 10^4$/ml. The cells were pre-incubated in an incubator at 37° C. in 5% $CO_2$ for 24 hours. The drug with 6 to 8 different concentrations was added and treated continuously for 48 h.

After the treatment of the drug, take photos by a phase contrast microscope. Then MTT treatment solution was added into each well and after 4 hours lysed the cells by DMSO. The OD values for each well were determined by using Plarstar ELIASA.

Test control: Add 20 μl culture solution into each blank control well, and use imatinib as a positive control.

Concentration setting: 5-8 concentrations within the range of 0.001-10 μM were set, and each concentration is set in triplicate.

4) The Evaluation of Therapeutic Effect

The calculation of the inhibition rate of cell grows:

$$\frac{OD_{control} - OD_{treatment}}{OD_{control}} \times 100\%$$

5) Results

Figure 2:
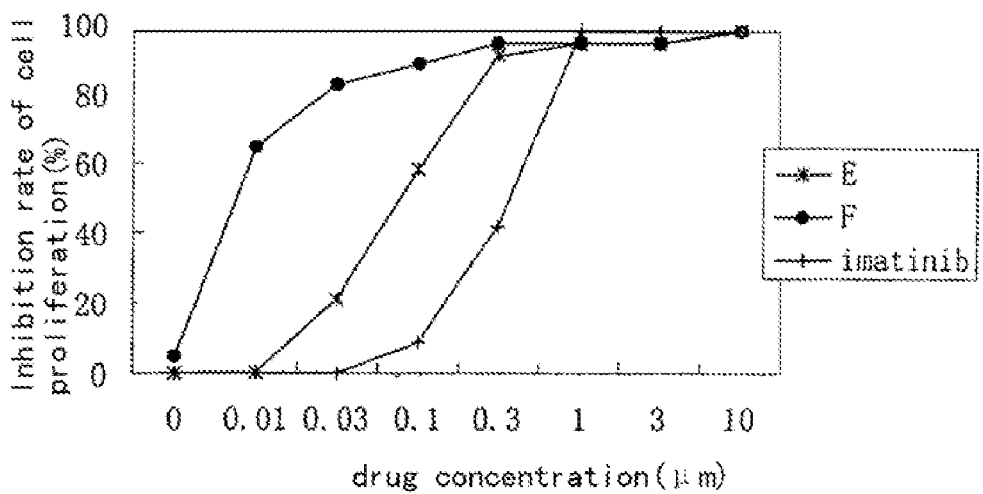
FIG. 2 shows the correlation of drug concentration of the aminopyrimidine compounds with the inhibition rate of the proliferation of human myeloid leukemia K562 cells.
Figure 3A:
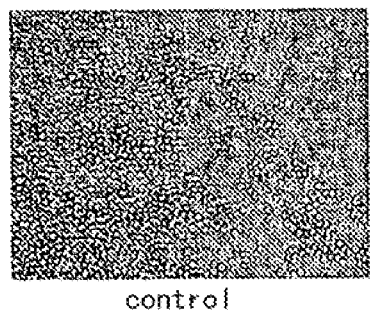
FIGS. 3a to 3h show the inhibition of aminopyrimidine compounds on the proliferation of human myeloid leukemia K562 cells and promyelocytic leukemia HL-60. Each diagram is described as below.
Figure 3B:
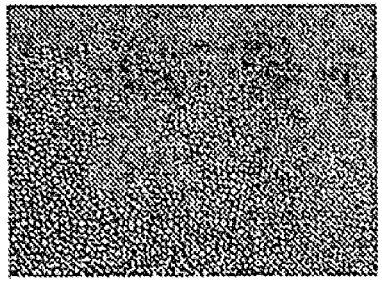
Figure 3C:
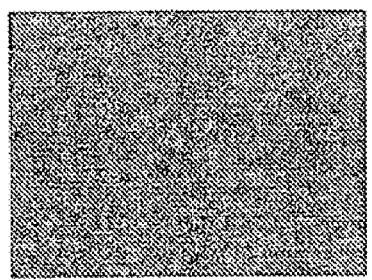
Figure 3D:
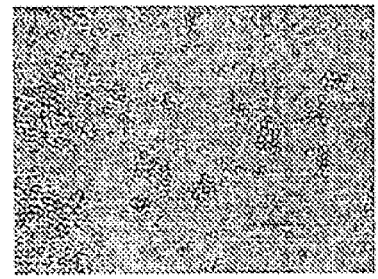
Figure 3E:
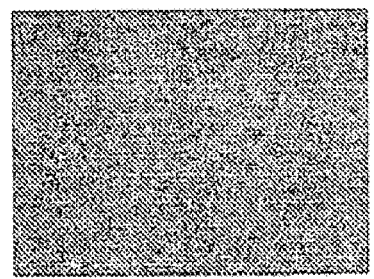
Figure 3F:
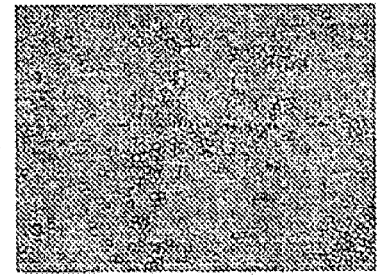
Figure 3G:
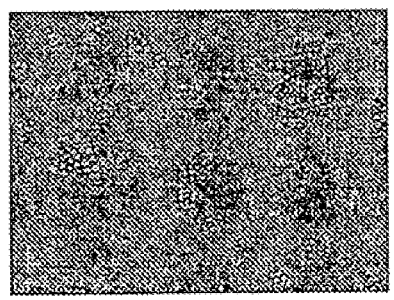
Figure 3H:
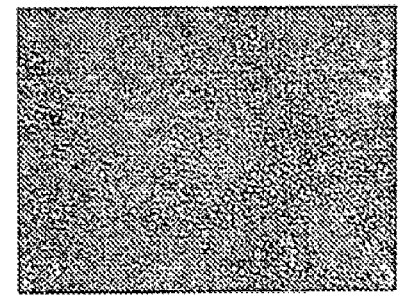

Imatinib inhibits the proliferation of cells through inhibiting the activity of Abl tyrosine kinase. Bcr-Abl fusion protein may be produced in more than 95% of chronic myelogenous leukemia patients due to chromosome translocation, resulting in the activity of high expression of Abl tyrosine kinase. Human chronic myelogenous leukemia K562 cell can express Bcr-Abl protein and thus, it is conventional cell model for the study of a drug directing to Bcr-Abl. It is found that the compounds of the present invention exhibited different extent of inhibition effects on the proliferation of K562 cells. The effect of compound F is about 40 times higher than imatinib. The effect of compound E is 4 times higher than imatinib. Human premyelocyte leukemia HL-60 cell does not express Bcr-Abl and thus, used as control model in this test. The results indicated that the compounds of the present invention do not influent the proliferation of HL-60 cell even in a high concentration (10 μM). This suggests that these compounds have excellent selectivity for the target. The selectivity of imatinib, compound F and compound E are approximately over 30, 1250 and 125 folds, respectively. In conclusion, compound E and F of the present invention exhibit strong inhibition effects on the proliferation of target leukemia cells with the effects superior than or equal to the control, Imtinib (results are presented in Table 1, FIGS. 1, 2, 3).

TABLE 1

The inhibition effects of aminopyrimidine compounds on the proliferation of leukemia cells cultured in vitro

| | $IC_{50}$ (μM) | | |
|---|---|---|---|
| | Compound E | Compound F | imatinib |
| K562 | 0.08 | 0.008 | 0.33 |
| HL-60 | >10 | 10 | >10 |

6) Conclusions

HH-GV-E and HH-GV-F exhibit strong inhibition effects on the proliferation of target leukemia cells with the effects superior than the control, Imtinib.

Test Example 2:

The Therapeutic Effect of HH-GV-E, HH-GV-F and Gleevec on Naked Mice with Transplant Tumor of Human Granulocytic Leukemia K562

HH-GV-E refers to 4-((4-methylpiperazin-1-yl)methyl)-N-[6-methyl-5-[[4-(pyrid-3-yl)pyrimidin-2-yl]amino]pyrid-3-yl]-3-chloro-benzamide methanesulfonic acid salt;

HH-GV-F refers to 4-((4-methylpiperazin-1-yl)methyl)-N-[6-methyl-5-[[4-(pyrid-3-yl)pyrimidin-2-yl]amino]pyrid-3-yl]-3-(trifluoromethyl)-benzamide methanesulfonic acid salt.

1) Experimental Animals

BALB/cA-nude mice were obtained from SHANGHAI SLAC LABORATORY ANIMAL CO.; 18-21 g, ♀, certificate number: SCXK (hu) 2004-0005; Fed in SPF environment of constant temperature and humidity.

2) Experimental Procedure

Animals were allowed to acclimatize the environment for one week, and then the animals were inoculated subcutaneously human leukemia K562 cells. When the tumors have grown to a volume of 100-300 $mm^3$, the animals were randomly grouped (d0). The naked mice were administered by oral gavage. The doses for HH-GV-E and Gleevec were both 75 mg/kg and 150 mg/kg; the doses for HH-GV-F were 37.5 mg/kg and 75 mg/kg. The animals were administered once per day for 21 days. Measured the volume of the tumors 2-3 times per week and weighed the animals followed by recording the data. The formula for calculating the volume of tumor (V): $V = \frac{1}{2} \times a \times b^2$, wherein a represents the length and b represents the width.

3) Results

The mice were continuously administered by oral gavage once per day for 21 days.

In the control group, on the Day 18, 1/8 of the mice were died, and at the end of the experiment, 2/8 of the mice were died. The death is considered to be caused by the growth of the tumor according to the observation of the growth of the tumor and the status of the mice.

According to the present protocol, Gleevec did not have significant effect on the growth of the tumor. On Day 18, 1/6 of the mice in 150 mg/kg group were died and the death is considered to be related to the tumor.

Administration of 150 mg/kg HH-GV-E has significant inhibition effect on the growth of K562 tumor.

Figure 4:
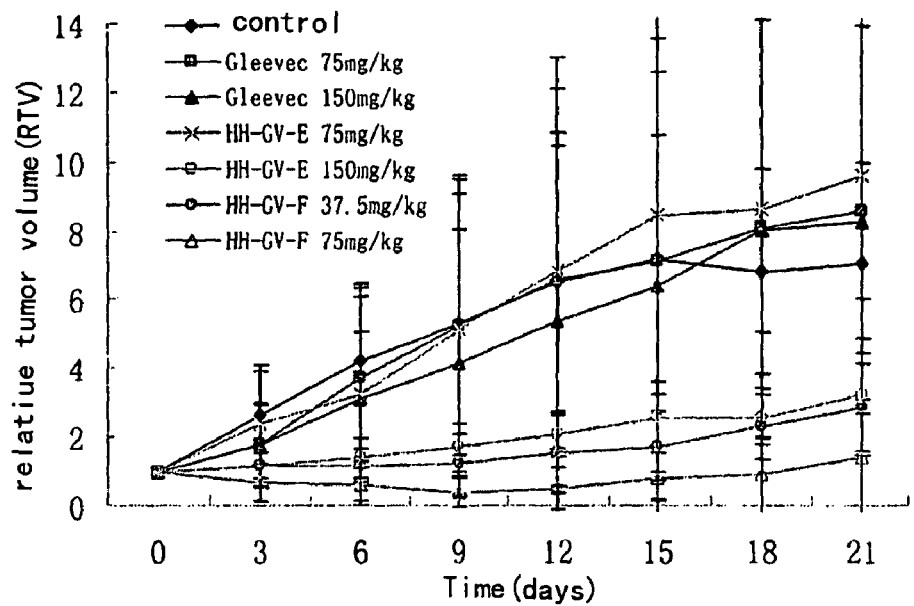
FIG. 4 shows the influence of HH-GV-E, HH-GV-F and Gleevec on naked mice with transplant tumors of human granulocytic leukemia K562.
Figure 5:
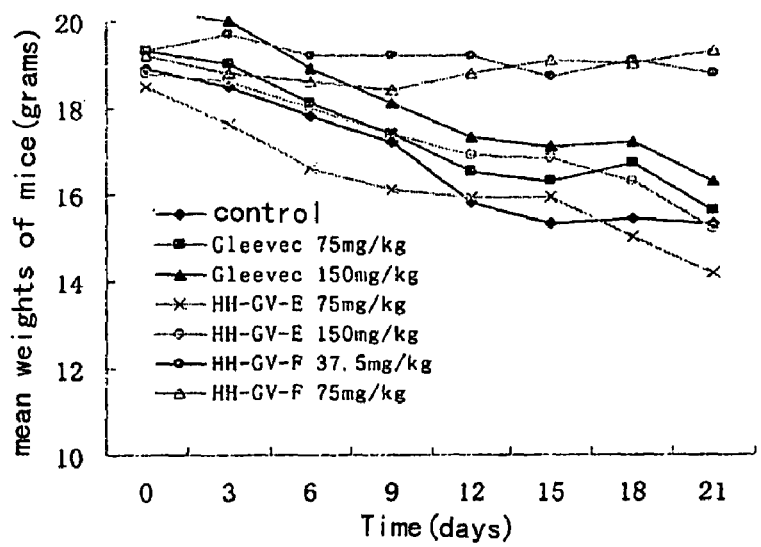
FIG. 5 shows the influence of HH-GV-E, HH-GV-F and Gleevec on the body weights of tumor-bearing naked mice.
Figure 6:
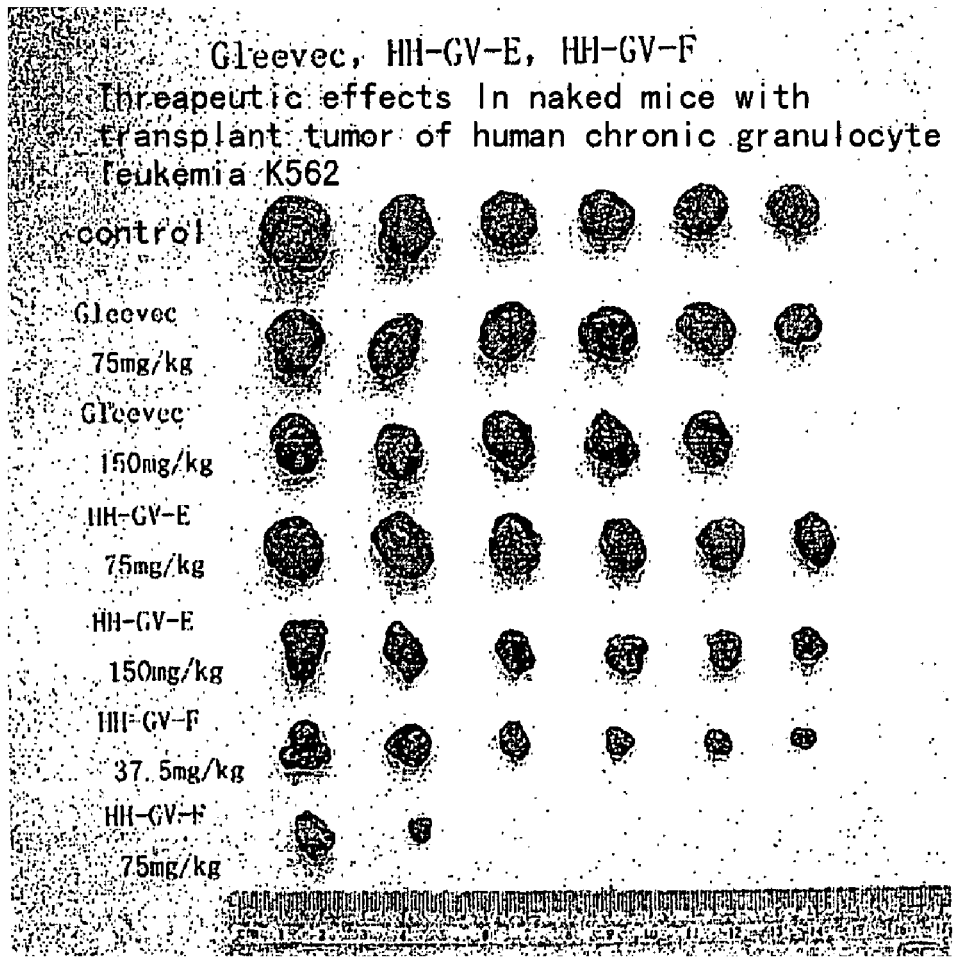
FIG. 6: photographs of tumors showing the therapeutic effects of HH-GV-E, HH-GV-F and Gleevec on naked mice with transplant tumors of human granulocytic leukemia K562.

In the HH-GV-F 75 mg/kg group, on Day 9, the tumor was extinct in one mouse (1/6); and on Day 12, the tumors were extinct in four mice (4/6); and on Day 15, the tumors were extinct in five mice (5/6). At the end of the experiment (i.e., Day 21), tumor was relapsed in one mouse. Thus, tumors were extinct in four mice (4/6) at the end of the experiment. Administration of 37.5 mg/kg significantly inhibited the growth of K562 tumor, but did not cause the tumor extinct. Thus, the therapeutic effect of HH-GV-F shows significant dose dependence. Since the tumors were extinct, the mice in HH-GV-F group had an apparently better status than those of Gleevec and HH-GV-E groups. This indicates that HH-GV-F has very good therapeutic effect on chronic granulocyte leukemia (results are presented in Table 2 and FIGS. 4, 5, 6).

1) Animals

BALB/cA-nude mice were obtained from SHANGHAI SLAC LABORATORY ANIMAL CO.; 5-6 weeks age, ♀, certificate number: SCXK (hu) 2004-0005; Fed in SPF environment of constant temperature and humidity.

2) Experimental Procedure

Animals were allowed to acclimatize the environment for one week, and then the animals were inoculated subcutaneously human leukemia K562 cells. When the tumors have grown to a volume of 100-300 mm$^3$, the animals were randomly grouped (d0). The naked mice were administered with HH-GV-678 and Gleevec by oral gavage. The doses for HH-GV-678 were 75 mg/kg and 150 mg/kg; the dose for Gleevec was 150 mg/kg. The animals were administered with HH-GV-678 once per day for 21 days, or the animals were administered with Gleevec twice per day for 21 days, with 150 mg/kg each time. Measured the volume of the tumors 2-3 times per week and weighed the animals followed by recording the data. The formula for calculating the volume of tumor (V): $V = 1/2 \times a \times b^2$, wherein a represents the length and b represents the width.

3) Results

In HH-GV-678 75 mg/kg group, on Day 6, complete extinction (complete resolution, CR) of tumors was found in 3 mice (3/8 of the group); and complete resolution of tumors was observed in 7 mice (7/8 of the group) on Day 9. On Day 12, all tumors were completely disappeared (8/8).

TABLE 2

The therapeutic effects of HH-GV-E, HH-GV-F and Gleevec administrated orally on naked mice with transplant tumor of human granulocytic leukemia K562

| Group | Dose (mg/kg) | Nos. of animals | | Body weight before dissection (gram) | | TV x ± SD | | RTV x ± SD | T/C (%) | CR |
|---|---|---|---|---|---|---|---|---|---|---|
| | | d0 | dn | d0 | dn | d0 | dn | | | |
| Control | | 8 | 6 | 18.9 | 16.3 | 161 ± 61 | 1133 ± 527 | 7.05 ± 2.91 | | 0/6 |
| Gleevec | 75 | 6 | 6 | 19.3 | 15.6 | 153 ± 68 | 971 ± 154 | 8.56 ± 7.09 | 121.0 | 0/6 |
| Gleevec | 150 | 6 | 5 | 20.3 | 16.3 | 127 ± 45 | 824 ± 170 | 8.30 ± 5.65 | 117.7 | 0/6 |
| HH-GV-E | 75 | 6 | 6 | 18.5 | 14.2 | 130 ± 58 | 954 ± 242 | 9.60 ± 6.51 | 103.6 | 0/6 |
| HH-GV-E | 150 | 6 | 6 | 18.8 | 15.2 | 149 ± 31 | 455 ± 214 | 3.24 ± 1.65 | 47.4* | 0/6 |
| HH-GV-F | 37.5 | 6 | 6 | 19.3 | 18.8 | 119 ± 51 | 294 ± 255 | 2.85 ± 3.18 | 40.4* | 0/6 |
| HH-GV-F | 75 | 6 | 6 | 19.2 | 19.3 | 127 ± 46 | 95 ± 199 | 1.38 ± 3.08 | 19.6* | 4/6 | d0: the time of grouping and first administration;
dn: day 21 after the first administration;
*P < 0.01 vs control;
CR: complete extinction (complete resolution) of tumor.

4) Conclusion

HH-GV-F and HH-GV-E have very good therapeutic effects on human granulocytic leukemia K562 with the effects significantly superior to Gleevec.

Test Example 3:

The Therapeutic Effects of HH-GV-678 and Gleevec on Naked Mice With Transplant Tumor of Human Granulocytic Leukemia K562

HH-GV-678 (i.e., HH-GV-F) refers to 4-((4-methylpiperazin-1-yl)methyl)-N-[6-methyl-5-[[4-(pyrid-3-yl)pyrimidin-2-yl]amino]pyrid-3-yl]-3-(trifluoromethyl)-benzamide methanesulfonic acid salt.

In HH-GV-678 150 mg/kg group, on Day 6, complete resolution (CR) of tumors was found in 6 mice (6/8 of the group); on Day 9, all tumors were completely disappeared (8/8 of the group).

In Gleevec group, on Day 12, complete resolution (CR) of tumor was found in one mouse (1/8 of the group); at the end of the experiment, complete resolution of tumors was observed only in two mice (2/8 of the group).

The experiment suggests that HH-GV-678 takes action more quickly than Gleevec; and the therapeutic effect of HH-GV-678 is significantly superior to that of Gleevec.

Figure 7:
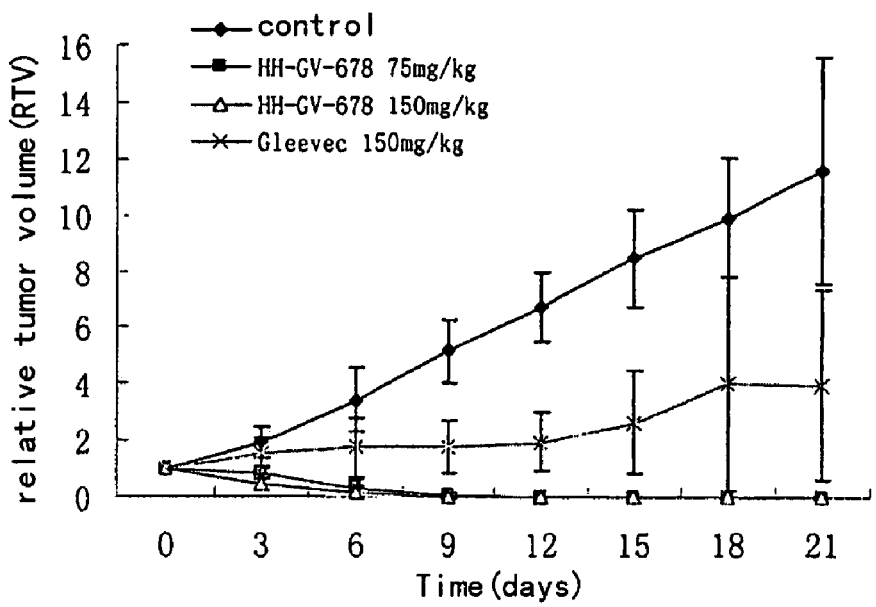
FIG. 7 shows the therapeutic effects of HH-GV-678, Gleevec on naked mice having transplant tumors of human granulocytic leukemia K562.
Figure 8:
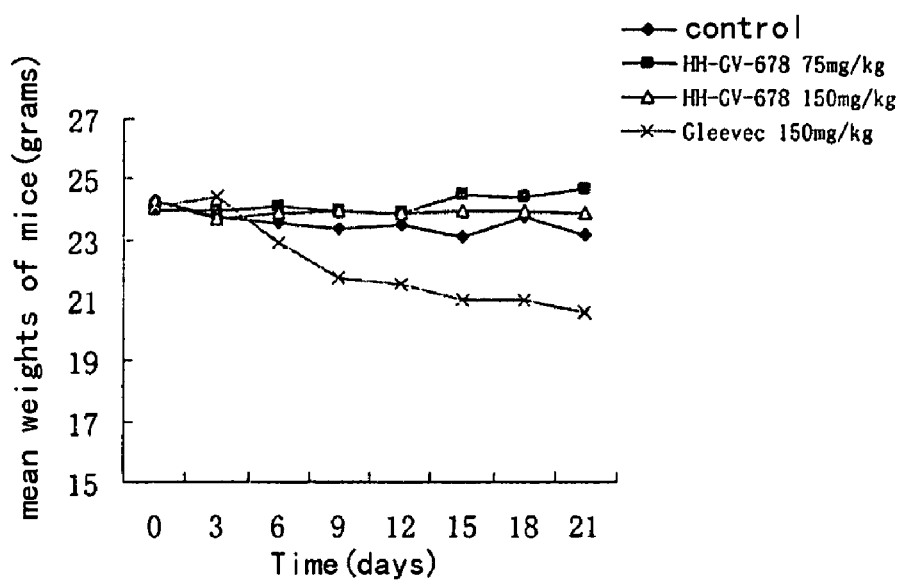
FIG. 8 shows the influence of HH-GV-678, Gleevec on the body weights of tumor-bearing naked mice.

Tumor-bearing mice show very good tolerance to both two compounds. The toxicity of HH-GV-678 is relatively lower under this experimental condition (results are presented in Table 3, and FIGS. 7, 8)

TABLE 3

The therapeutic effects of HH-GV-678 and Gleevec administrated orally on naked mice with transplant tumor of human granulocytic leukemia K562

| group | Dose (mg/kg) | Nos. Of animal d0 | dn | Body weight before dissection (gram) d0 | dn | TV x ± SD d0 | dn | RTV x ± SD | T/C (%) | CR |
|---|---|---|---|---|---|---|---|---|---|---|
| control |  | 11 | 11 | 17.3 | 14.2 | 181 ± 52 | 1995 ± 646 | 11.59 ± 4.04 |  | 0/8 |
| HH-GV-678 | 75 | 8 | 8 | 24.0 | 24.7 | 168 ± 65 | 0 ± 0 | 0 ± 0 | 0* | 7/8 |
| HH-GV-678 | 150 | 8 | 8 | 24.3 | 23.9 | 152 ± 37 | 0 ± 0 | 0 ± 0 | 0* | 8/8 |
| Gleevec | 150 | 8 | 8 | 24.1 | 20.6 | 144 ± 33 | 501 ± 347 | 3.96 ± 3.38 | 34.2* | 2/8 | d0: the time of grouping and first administration;
dn: day 21 after the first administration;
*P < 0.01 vs control;
CR: complete resolution.

4) Conclusion

Both HH-GV-678 and Gleevec have significant therapeutic effects on human granulocytic leukemia K562; the therapeutic effect of HH-GV-678 is significantly superior to that of Gleevec; the toxicity of HH-GV-678 is relatively lower than that of Gleevec under this experimental condition.

What is claimed is:

1. An aminopyrimidine compound of general formula (I) or pharmaceutically acceptable salts thereof:

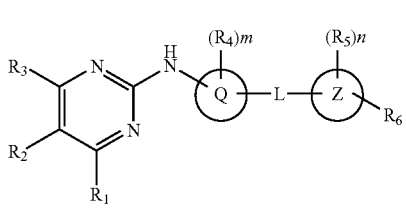

(I)

wherein, $R_1$ is selected from substituted or unsubstituted aryl, heteroaryl, or heterocycle, in which the substituent is selected from halogen, $C_{1-4}$ linear or branched alkyl, amino, alkoxy or cycloalkyl;

$R_2$ and $R_3$ are independently selected from hydrogen, halogen, amino, alkylamino, dialkylamino, cyano, nitro, hydroxy, alkoxy, haloalkoxy; or substituted or unsubstituted alkyl, cycloalkyl, alkenyl, alkynyl, aryl, heteroaryl, arylalkyl or heteroarylalkyl, in which the substituent is selected from halogen, $C_{1-4}$ linear or branched alkyl, amino, alkoxy or nitro;

$R_4$ is selected from hydrogen, halogen, amino, alkylamino, dialkylamino, cyano; or substituted or unsubstituted alkyl, cycloalkyl, alkenyl, alkynyl, in which the substituent is selected from halogen, amino or hydroxy;

$R_5$ is selected from hydrogen, halogen, nitro, cyano, hydroxy, alkoxy, methylenedioxy, haloalkoxy, amino; or substituted or unsubstituted alkyl, cycloalkyl, alkenyl, alkynyl, aryl or heteroaryl, in which the substituent is selected from halogen, amino or hydroxy;

$R_6$ is selected from hydrogen, or substituted or unsubstituted alkyl, cycloalkyl, aryl, arylalkyl, heteroaryl, heteroarylalkyl, heterocycle, heterocyclic alkyl, in which the substituent is selected from halogen, amino or $C_{1-4}$ alkyl;

m=0, 1, 2 or 3;
n=0, 1, 2 or 3;
Q is pyridyl;

Z is selected from aryl, heteroaryl or heterocycle;

L is selected from —NR$_7$CO—, —CONR$_8$—, —NR$_9$SO$_2$—, —SO$_2$NR$_{10}$—, NR$_{11}$COO—, —NR$_{12}$CONR$_{13}$—, —OCONR$_{14}$—; wherein $R_7$, $R_8$, $R_9$, $R_{10}$, $R_{11}$, $R_{12}$, $R_{13}$ and $R_{14}$ are independently selected from hydrogen, substituted or unsubstituted alkyl, substituted or unsubstituted cycloalkyl, in which the substituent is selected from halogen, amino or hydroxyl.

2. The compound of claim 1 or pharmaceutically acceptable salts thereof, wherein $R_1$ is selected from substituted or unsubstituted heteroaryl, wherein the substituent is selected from halogen, $C_{1-4}$ linear or branched alkyl.

3. The compound of claim 1 or pharmaceutically acceptable salts thereof, wherein $R_2$ and $R_3$ are independently selected from hydrogen, halogen, amino, alkylamino, cyano, nitro; substituted or unsubstituted alkyl, cycloalkyl, wherein the substituent is hydrogen or halogen, wherein halogen refers to fluorine, chlorine, bromine, iodine.

4. The compound of claim 1 or pharmaceutically acceptable salts thereof, wherein $R_4$ is selected from substituted or unsubstituted alkyl, alkenyl, alkynyl, wherein the substituent is selected from halogen or amino.

5. The compound of claim 1 or pharmaceutically acceptable salts thereof, wherein $R_5$ is selected from hydrogen, halogen, nitro; substituted or unsubstituted alkyl, cycloalkyl, alkenyl, alkynyl; wherein the substitutent is selected from halogen or hydroxyl.

6. The compound of claim 1 or pharmaceutically acceptable salts thereof, wherein $R_6$ is selected from substituted or unsubstituted heteroaryl, heteroarylalkyl, heterocycle, and heterocyclylalkyl, wherein $C_{1-4}$ alkyl and cycloalkyl are the preferred substitutents.

7. The compound of claim 1 or pharmaceutically acceptable salts thereof, wherein m and n are independently selected from 0, 1, 2 or 3.

8. The compound of claim 1 or pharmaceutically acceptable salts thereof, wherein Z is selected from aryl, heteroaryl or heterocycle.

9. The compound of claim 4 or pharmaceutically acceptable salts thereof, wherein $R_4$ is selected from substituted or unsubstituted $C_{1-4}$ alkyl and cycloalkyl.

10. The compound of claim 1 or pharmaceutically acceptable salts thereof, wherein L is selected from (1) —NR$_7$CO—, (2) —CONR$_8$—, (3) —NR$_9$SO$_2$—, (4) —SO$_2$NR$_{10}$—, (5) —NR$_{11}$COO—; in which, $R_7$, $R_8$, $R_9$, $R_{10}$ or $R_{11}$ is hydrogen.

11. The compound of claim 1 or pharmaceutically acceptable salts thereof, wherein the compound may be existed in single enantiomer form of (R), (S), (RS) or (SS), or in enantiomer-enriched form, or the salts thereof.

12. The compound of claim 1 or pharmaceutically acceptable salts thereof, wherein said compound forms a salt with an acid which is selected from organic acid or inorganic acid.

13. The compound of claim 12 or pharmaceutically acceptable salts thereof, wherein said organic acid is selected from acetic acid, trichloroacetic acid, propanoic acid, butanoic acid, aspartic acid, para-toluenesulfonic acid, maleic acid, and lactic acid; and said inorganic acid is selected from hydrochloric acid, sulfuric acid, phosphoric acid and methanesulfonic acid.

14. The compound of claim 12 or pharmaceutically acceptable salts thereof, wherein said acid is hydrochloric acid or methanesulfonic acid.

15. The compound of claim 11 or pharmaceutically acceptable salts thereof, wherein said compound forms a salt with equivalent amount of an acid.

16. The compound of claim 1 or pharmaceutically acceptable salts thereof, wherein said compound forms a salt with a base, and said salt is selected from alkali metals, alkaline earth metals and quaternary ammonium.

17. The compound of claim 16 or pharmaceutically acceptable salts thereof, wherein said quaternary ammonium is $NY_4$, wherein Y is $C_{1-4}$ alkyl.

18. The compound of claim 1 or pharmaceutically acceptable salts thereof, wherein said compound comprises the following compounds:
    4-[(4-methylpiperazin-1-yl)methyl]-N-{6-methyl-5-[(4-(pyrid-3-yl)pyrimid-2-yl)amino]pyrid-3-yl}benzamide;
    4-[(4-ethylpiperazin-1-yl)methyl]-N-{6-methyl-5-[(4-(pyrid-3-yl)pyrimid-2-yl)amino]pyrid-3-yl}benzamide;
    4-[(4-methylpiperazin-1-yl)methyl]-N-{6-methyl-5-[(4-(pyrid-3-yl)pyrimid-2-yl)amino]pyrid-3-yl}-3-fluorobenzamide;
    4-[(4-methylpiperazin-1-yl)methyl]-N-{6-methyl-5-[(4-(pyrid-3-yl)pyrimid-2-yl)amino]pyrid-3-yl}-3-chlorobenzamide;
    4-[(4-methylpiperazin-1-yl)methyl]-N-{6-methyl-5-[(4-(pyrid-3-yl)pyrimid-2-yl)amino]pyrid-3-yl}-3-(trifluoromethyl)benzamide;
    6-methyl-N-{3-(4-methyl-1H-imidazol-1-yl)-5-(trifluoromethyl)phenyl}-5-[4-(pyrid-3-yl)-2-(pyrimidyl)amino]nicotin;
    6-methyl-N-{4-[(4-methylpiperazin-1-yl)methyl]-3-(trifluoromethyl)phenyl}-5-[4-(pyrid-3-yl)-2-(pyrimidyl)amino]nicotin;
    4-[(4-methylpiperazin-1-yl)methyl]-N-{5-methyl-4-[(4-(pyrid-3-yl)-2-(pyrimidyl)amino)pyrid-2-yl]-3-(trifluoromethyl)benzamide;
    5-methyl-N-[4-(4-methylpiperazin-1-yl)methyl-3-(trifluoromethyl)phenyl]-4-[4-(pyrid-3-yl)-2-(pyrimidyl)amino]pyridinecarboxamide;
    5-methyl-N-[3-(4-methyl-1H-imidazol-1-yl)-5-(trifluoromethyl)phenyl]-4-[4-(pyrid-3-yl)-2-(pyrimidyl)amino]pyridinecarboxamide.

19. The compound of claim 2 or pharmaceutically acceptable salts thereof, wherein $R_1$ is selected from substituted or unsubstituted 6-memebered heteroaryl.

20. The compound of claim 19 or pharmaceutically acceptable salts thereof, wherein $R_1$ is selected from substituted or unsubstituted pyridinyl ring.

21. A method for the preparation of the compound of claim 1 or pharmaceutically acceptable salts thereof, wherein said method comprises the following steps:

(A) A compound of general formula (II) reacts with a compound of general formula (III) in basic condition to afford a compound of general formula (IV):

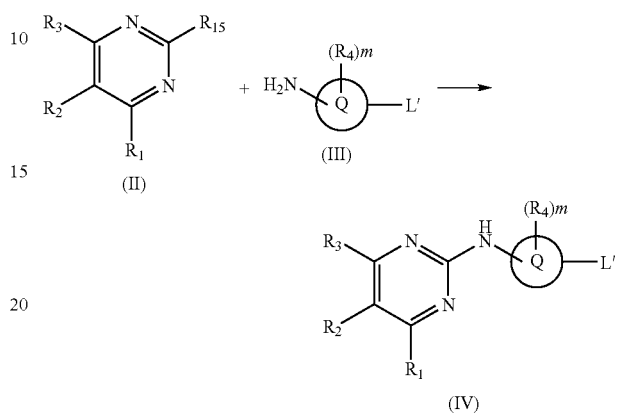

(B) Condensation reaction between the compound of general formula (IV) and a compound of general formula (V) in the presence of a condensation reagent to afford a compound of general formula (I),

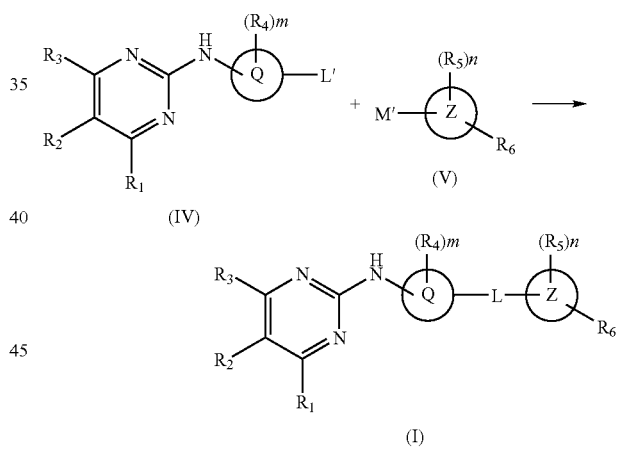

wherein $R_1$, $R_2$, $R_3$, $R_4$, $R_5$, $R_6$, Q, L, m, n are defined as claim 1; L', M' represent groups that allow condensation reaction occurred between them, which are amino, carboxyl, acid anhydride group, ester group, carboxylhalide group; or organic groups which can be converted into amino, carboxyl or carboxylhalide group by conventional methods, and $R_{15}$ represents an easily removable group, which is selected from halogen or methylsulfonyl, ethylsulfonyl, or p-methylbenzenesulfonyl.

22. The method of claim 21, wherein said organic group is nitro or ester group.

23. The method of claim 21, wherein:

(A) the base used in the preparation of the compound of general formula (IV) is selected from organic base or inorganic base, and said organic base is n-butyllithium, sodium methoxide, sodium ethoxide or potassium tert-butoxide; and said inorganic base is sodium hydroxide, potassium hydroxide, sodium amide or sodium hydride;

(B) in the preparation of the compound of general formula (I), in the case of condensation reaction occurred between carboxyl and amino, the condensation reagent is selected from N,N-dicyclohexylcarbodiimide, N,N-diisopropylcarbodiimide, N,N-diethylcarbodiimide, mixture of triphenylphosphine and diethyl azodicarboxylate, and mixture of triphenylphosphine and diisopropyl azodicarboxylate; in the case of condensation reaction occurred between carboxylhalide group and amino, the condensation reagent is selected from inorganic base or organic base.

24. The method of claim 21, wherein in the preparation of the compound (I), said inorganic base is selected from sodium carbonate, potassium carbonate and calcium carbonate, and said organic base is selected from triethylamine, pyridine, 4-dimethylaminopyridine, tripropylamine and tributylamine.

25. A pharmaceutical composition comprising the therapeutically effective amount of the compound of claim 1 or the pharmaceutically acceptable salt thereof and pharmaceutical acceptable carriers.

26. A method for treating chronic myelogenous leukemia with the compound of claim 1 or the pharmaceutically acceptable salts thereof, comprising the step of administration of an effective amount of the compound of claim 1 or the pharmaceutically acceptable salt thereof to a patient in need of such treatment.

27. The method of claim 26, wherein said compound is used independently or in combination with other pharmaceutical compounds.

* * * * *